US008722940B2

(12) United States Patent
Kauffman et al.

(10) Patent No.: US 8,722,940 B2
(45) Date of Patent: May 13, 2014

(54) HIGH MOLYBDENUM MIXED METAL OXIDE CATALYSTS FOR THE PRODUCTION OF UNSATURATED ALDEHYDES FROM OLEFINS

(75) Inventors: James W. Kauffman, Katy, TX (US); David L. Sullivan, Sugar Land, TX (US); Joe D. Dostal, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 13/410,242

(22) Filed: Mar. 1, 2012

(65) Prior Publication Data

US 2013/0231507 A1 Sep. 5, 2013

(51) Int. Cl.
C07C 45/34 (2006.01)
B01J 21/10 (2006.01)

(52) U.S. Cl.
USPC ........... 568/471; 568/476; 568/477; 502/243; 502/307

(58) Field of Classification Search
USPC ............... 568/471, 476, 477; 502/243, 307
See application file for complete search history.

(56) References Cited

U.S. PATENT DOCUMENTS

| | | | |
|---|---|---|---|
| 3,907,712 A | 9/1975 | Ohara et al. | 502/243 |
| 3,928,462 A | 12/1975 | Shiraishi et al. | 568/480 |
| 3,929,899 A | 12/1975 | Grasselli et al. | 568/476 |
| 3,933,751 A | 1/1976 | Callahan et al. | 568/477 |
| 3,936,505 A | 2/1976 | Oda et al. | 502/215 |
| 3,946,081 A | 3/1976 | Wedemeyer et al. | 568/470 |
| 3,954,856 A | 5/1976 | Kobayashi et al. | 562/538 |
| 3,956,181 A | 5/1976 | Grasselli et al. | 502/212 |
| 3,956,378 A | 5/1976 | Grasselli et al. | 562/546 |
| 3,959,384 A | 5/1976 | Takenaka et al. | 568/479 |
| 3,963,645 A | 6/1976 | Gelbein | 502/248 |
| 3,966,823 A | 6/1976 | Takenaka et al. | 568/479 |
| 3,972,920 A | 8/1976 | Ishii et al. | 562/538 |
| 3,980,709 A | 9/1976 | Kubo et al. | 568/479 |
| 3,984,477 A | 10/1976 | Kubo et al. | 568/479 |
| 3,993,673 A | 11/1976 | McMullen | 549/531 |
| 4,001,317 A | 1/1977 | Grasselli et al. | 562/546 |
| 4,012,449 A | 3/1977 | Shikakura et al. | 568/471 |
| 4,025,565 A | 5/1977 | Oda et al. | 568/477 |
| 4,034,008 A | 7/1977 | Kutz et al. | 562/546 |
| 4,035,418 A | 7/1977 | Okada et al. | 562/538 |
| 4,040,978 A | 8/1977 | Li | 502/212 |
| 4,045,478 A | 8/1977 | Umemura et al. | 562/535 |
| 4,049,577 A | 9/1977 | Childress et al. | 502/178 |
| 4,052,450 A | 10/1977 | Krabetz et al. | 562/546 |
| 4,052,462 A | 10/1977 | Sakakibara et al. | 568/477 |
| 4,060,545 A | 11/1977 | Miller et al. | 560/208 |
| 4,065,507 A | 12/1977 | Hardman et al. | 568/477 |
| 4,066,704 A | 1/1978 | Harris et al. | 568/475 |
| 4,078,004 A | 3/1978 | Schlaefer et al. | 568/479 |
| 4,087,382 A | 5/1978 | Khoobiar | 502/249 |
| 4,111,984 A | 9/1978 | Ishii et al. | 562/538 |
| 4,111,985 A | 9/1978 | Okada et al. | 562/546 |
| 4,118,419 A | 10/1978 | Ishii et al. | 562/534 |
| 4,124,634 A | 11/1978 | Gotoh et al. | 562/532 |
| 4,127,603 A | 11/1978 | Bljumberg et al. | 562/533 |
| 4,129,600 A | 12/1978 | Childress et al. | 568/479 |
| 4,134,859 A | 1/1979 | Kurtz et al. | 502/249 |
| 4,148,757 A | 4/1979 | Brazdil et al. | 502/205 |
| 4,151,117 A | 4/1979 | Schlaefer | 502/212 |
| 4,155,938 A | 5/1979 | Yamamoto et al. | 568/479 |
| 4,162,234 A | 7/1979 | Grasselli et al. | 502/205 |
| 4,166,808 A | 9/1979 | Daumas et al. | 502/249 |
| 4,170,570 A | 10/1979 | Zagata et al. | 502/211 |
| 4,171,328 A | 10/1979 | Umemura et al. | 568/479 |
| 4,171,454 A | 10/1979 | Miller et al. | 562/546 |
| 4,174,354 A | 11/1979 | Grasselli et al. | 585/626 |
| 4,174,459 A | 11/1979 | Sakamoto et al. | 562/534 |
| 4,176,234 A | 11/1979 | Grasselli et al. | 562/546 |
| 4,180,678 A | 12/1979 | Wada et al. | 562/534 |
| 4,182,907 A | 1/1980 | Grasselli et al. | 562/546 |
| 4,184,981 A | 1/1980 | Vanderspurt | 502/209 |
| 4,186,152 A | 1/1980 | Yamamoto et al. | 568/477 |
| 4,190,608 A | 2/1980 | Grasselli et al. | 562/546 |
| 4,195,187 A | 3/1980 | Vanderspurt | 562/545 |
| 4,205,181 A | 5/1980 | Murib | 560/241 |
| 4,208,303 A | 6/1980 | Sasaki et al. | 502/38 |
| 4,209,640 A | 6/1980 | Yamamoto et al. | 562/532 |
| 4,212,767 A | 7/1980 | Daniel | 502/211 |
| 4,217,309 A | 8/1980 | Umemura et al. | 568/477 |
| 4,219,670 A | 8/1980 | Okada et al. | 562/546 |
| 4,224,187 A | 9/1980 | Vanderspurt | 502/212 |
| 4,224,193 A | 9/1980 | Vanderspurt | 502/307 |
| 4,225,466 A | 9/1980 | Wada et al. | 502/209 |
| 4,230,639 A | 10/1980 | Khoobiar | 568/471 |
| 4,230,640 A | 10/1980 | Khoobiar | 568/477 |
| 4,240,931 A | 12/1980 | Milberger et al. | 502/306 |

(Continued)

FOREIGN PATENT DOCUMENTS

| | | | | |
|---|---|---|---|---|
| EP | 0 025 715 B1 | 3/1981 | | C07C 27/14 |
| EP | 0 169 449 B1 | 1/1986 | | C07C 47/22 |

(Continued)

OTHER PUBLICATIONS

PCT Written Opinion, Apr. 11, 2013.

(Continued)

Primary Examiner — Sikarl Witherspoon
(74) Attorney, Agent, or Firm — Cantor Colburn LLP

(57) ABSTRACT

A catalyst for the oxidation of an olefin to an unsaturated aldehyde comprising a mixed metal oxide having the formula (I):

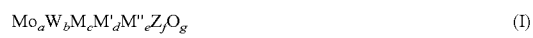

$$Mo_aW_bM_cM'_dM''_eZ_fO_g \qquad (I)$$

where M represents trivalent metals, M' represents divalent metals, M" represents monovalent metals, Z represents elements in the form of an oxide, a, b, c, d, e, f and g are numbers, and where the catalyst has an anion to cation molar (ACM) ratio greater than 1.00 and less than 2.00 and an M' to M molar ratio between 1.95 and 2.15.

38 Claims, 5 Drawing Sheets

(56) References Cited

U.S. PATENT DOCUMENTS

| | | | |
|---|---|---|---|
| 4,245,118 A | 1/1981 | Yamamoto et al. | 562/532 |
| 4,248,803 A | 2/1981 | Vanderspurt | 568/477 |
| 4,250,339 A | 2/1981 | Sakamoto et al. | 568/471 |
| 4,252,683 A | 2/1981 | Khoobiar | 502/211 |
| RE30,545 E | 3/1981 | Khoobiar | 502/249 |
| 4,258,217 A | 3/1981 | Aoshima et al. | 568/474 |
| 4,261,858 A | 4/1981 | Khoobiar | 502/211 |
| 4,267,385 A | 5/1981 | Umemura et al. | 568/479 |
| 4,267,386 A | 5/1981 | Vanderspurt | 568/480 |
| 4,271,040 A | 6/1981 | Khoobiar | 502/211 |
| 4,272,408 A | 6/1981 | Daniel | 502/211 |
| 4,272,637 A | 6/1981 | Yamamoto et al. | 568/780 |
| 4,276,196 A | 6/1981 | Dalton et al. | 502/212 |
| 4,280,928 A | 7/1981 | Kirch et al. | 502/205 |
| 4,280,929 A | 7/1981 | Shaw et al. | 502/215 |
| 4,292,203 A | 9/1981 | Milberger et al. | 502/304 |
| 4,297,247 A | 10/1981 | Krabetz et al. | 502/310 |
| 4,298,763 A | 11/1981 | Engelbach et al. | 568/479 |
| 4,303,550 A | 12/1981 | Callahan et al. | 502/24 |
| 4,306,088 A | 12/1981 | Nakamura et al. | 568/471 |
| 4,306,090 A | 12/1981 | Kirch et al. | 568/481 |
| 4,311,611 A | 1/1982 | Sasaki et al. | 502/22 |
| 4,316,856 A | 2/1982 | Guttmann et al. | 558/322 |
| 4,320,227 A | 3/1982 | Matsumoto et al. | 562/534 |
| 4,321,160 A | 3/1982 | Farrington et al. | 502/209 |
| 4,323,703 A | 4/1982 | Grasselli et al. | 562/546 |
| 4,332,971 A | 6/1982 | Dalton et al. | 568/480 |
| 4,337,364 A | 6/1982 | Solomon | 568/475 |
| 4,339,355 A | 7/1982 | Decker et al. | 502/343 |
| 4,341,900 A | 7/1982 | Ishii et al. | 562/532 |
| 4,351,963 A | 9/1982 | Ray et al. | 568/477 |
| 4,354,044 A | 10/1982 | Aoshima et al. | 568/479 |
| 4,356,316 A | 10/1982 | Aoshima et al. | 560/208 |
| RE31,088 E | 11/1982 | Grasselli et al. | 562/535 |
| 4,370,490 A | 1/1983 | Gruber et al. | 560/214 |
| 4,374,759 A | 2/1983 | Khoobiar | 502/249 |
| 4,377,501 A | 3/1983 | Khoobiar | 502/211 |
| 4,380,664 A | 4/1983 | Ishii et al. | 562/546 |
| 4,388,223 A | 6/1983 | Ferlazzo et al. | 502/211 |
| 4,388,225 A | 6/1983 | Solomon | 502/346 |
| 4,397,771 A | 8/1983 | Grasselli et al. | 502/306 |
| 4,404,397 A | 9/1983 | Daniel | 562/546 |
| 4,413,147 A | 11/1983 | Khoobiar | 568/476 |
| 4,414,134 A | 11/1983 | Friedrich et al. | 502/204 |
| 4,415,482 A | 11/1983 | Ebner | 502/205 |
| 4,419,270 A | 12/1983 | Ueshima et al. | 502/209 |
| 4,424,141 A | 1/1984 | Grasselli et al. | 502/205 |
| 4,425,255 A | 1/1984 | Toyoda et al. | 502/38 |
| 4,442,308 A | 4/1984 | Arntz et al. | 568/480 |
| 4,443,555 A | 4/1984 | Callahan et al. | 502/211 |
| 4,443,556 A | 4/1984 | Aoki et al. | 502/212 |
| 4,444,906 A | 4/1984 | Callahan et al. | 502/211 |
| 4,444,907 A | 4/1984 | Ohdan et al. | 502/211 |
| 4,446,328 A | 5/1984 | Aoshima et al. | 568/479 |
| 4,453,006 A | 6/1984 | Shaw et al. | 562/545 |
| 4,454,346 A | 6/1984 | Khoobiar | 562/535 |
| 4,467,113 A | 8/1984 | Matsumoto et al. | 562/535 |
| 4,471,061 A | 9/1984 | Shaw et al. | 502/34 |
| 4,471,062 A | 9/1984 | Farrington et al. | 502/34 |
| 4,479,013 A | 10/1984 | Khoobiar | 568/479 |
| 4,489,170 A | 12/1984 | Krabetz et al. | 502/211 |
| 4,499,301 A | 2/1985 | Murib | 562/546 |
| 4,503,247 A | 3/1985 | Khoobair | 562/535 |
| 4,511,671 A | 4/1985 | Saito et al. | 502/242 |
| 4,518,523 A | 5/1985 | Blum et al. | 502/209 |
| 4,528,398 A | 7/1985 | Callahan et al. | 562/534 |
| 4,530,916 A | 7/1985 | Matsumoto et al. | 502/209 |
| 4,532,365 A | 7/1985 | Khoobiar | 568/479 |
| 4,535,188 A | 8/1985 | Khoobiar | 568/479 |
| 4,537,874 A | 8/1985 | Sato et al. | 502/311 |
| 4,537,998 A | 8/1985 | Shum et al. | 568/483 |
| 4,547,588 A | 10/1985 | Khoobiar | 562/535 |
| 4,552,860 A | 11/1985 | Murib | 502/242 |
| 4,556,731 A | 12/1985 | Guttmann et al. | 562/546 |
| 4,558,028 A | 12/1985 | Tsuneki et al. | 502/211 |
| 4,558,029 A | 12/1985 | Paparizos et al. | 502/211 |
| 4,558,154 A | 12/1985 | Shum et al. | 562/537 |
| RE32,082 E | 2/1986 | Khoobiar | 568/476 |
| 4,585,883 A | 4/1986 | Briggs | 556/42 |
| 4,596,784 A | 6/1986 | Kennelly et al. | 502/209 |
| 4,621,155 A | 11/1986 | Ueshima et al. | 562/534 |
| 4,652,673 A | 3/1987 | Matsumoto et al. | 562/535 |
| 4,677,084 A | 6/1987 | Bergna | 502/8 |
| 4,720,575 A | 1/1988 | Gruber | 560/214 |
| 4,732,884 A | 3/1988 | Sarumaru et al. | 502/205 |
| 4,778,930 A | 10/1988 | Grasselli et al. | 568/477 |
| 4,803,190 A | 2/1989 | Sarumaru et al. | 502/205 |
| 4,816,603 A | 3/1989 | Oh-Kita et al. | 562/538 |
| 4,855,275 A | 8/1989 | Suresh et al. | 502/353 |
| 4,871,700 A | 10/1989 | Uchida et al. | 502/51 |
| 4,916,103 A | 4/1990 | Martan et al. | 502/212 |
| 4,925,823 A | 5/1990 | Krabetz et al. | 502/211 |
| 4,946,819 A | 8/1990 | Sasaki et al. | 502/214 |
| 4,954,650 A | 9/1990 | Abe et al. | 562/534 |
| 4,968,846 A | 11/1990 | Kuragano et al. | 568/479 |
| 4,985,592 A | 1/1991 | Ishii et al. | 562/534 |
| 5,017,542 A | 5/1991 | Martan et al. | 502/209 |
| 5,059,573 A | 10/1991 | Sasaki et al. | 502/205 |
| 5,072,052 A | 12/1991 | Boeck et al. | 568/479 |
| 5,081,314 A | 1/1992 | Kissel et al. | 568/479 |
| 5,082,819 A | 1/1992 | Boeck et al. | 502/212 |
| 5,094,990 A | 3/1992 | Sasaki et al. | 502/214 |
| 5,102,847 A | 4/1992 | Yamamoto et al. | 502/209 |
| 5,132,269 A | 7/1992 | Sasaki et al. | 502/205 |
| 5,138,100 A | 8/1992 | Matsuura | 568/474 |
| 5,139,988 A | 8/1992 | Sasaki et al. | 502/206 |
| 5,144,090 A | 9/1992 | Honda et al. | 568/476 |
| 5,153,162 A | 10/1992 | Kurimoto et al. | 502/209 |
| 5,155,262 A | 10/1992 | Etzkorn et al. | 562/532 |
| 5,166,119 A | 11/1992 | Oh-Kita et al. | 502/205 |
| 5,166,199 A | 11/1992 | Kasch et al. | |
| 5,173,468 A | 12/1992 | Boehning et al. | 502/209 |
| 5,183,936 A | 2/1993 | Etzkorn et al. | 562/532 |
| 5,198,578 A | 3/1993 | Etzkorn et al. | 562/532 |
| 5,198,581 A | 3/1993 | Kawajiri et al. | 562/546 |
| 5,206,431 A | 4/1993 | Hashiba et al. | 562/534 |
| 5,208,371 A | 5/1993 | Kuroda et al. | 562/538 |
| 5,218,146 A | 6/1993 | Takata et al. | 562/535 |
| 5,221,653 A | 6/1993 | Jaeger et al. | 502/212 |
| 5,221,767 A | 6/1993 | Boehning et al. | 562/532 |
| 5,225,389 A | 7/1993 | Caillod et al. | 502/205 |
| 5,235,088 A | 8/1993 | Paparizos et al. | |
| 5,245,083 A | 9/1993 | Matsuura | 568/479 |
| 5,250,485 A | 10/1993 | Kuroda et al. | 502/159 |
| 5,264,627 A | 11/1993 | Tazaki et al. | 562/599 |
| 5,276,178 A | 1/1994 | Onodera et al. | 562/537 |
| 5,300,707 A | 4/1994 | Caillod et al. | 568/480 |
| 5,349,092 A | 9/1994 | Watanabe et al. | 568/480 |
| 5,364,825 A | 11/1994 | Neumann et al. | 502/311 |
| 5,380,933 A | 1/1995 | Ushikubo et al. | 562/549 |
| 5,491,258 A | 2/1996 | Watanabe et al. | 562/538 |
| 5,532,199 A | 7/1996 | Watanabe et al. | 502/311 |
| 5,602,280 A | 2/1997 | Nagai et al. | 562/546 |
| 5,618,974 A | 4/1997 | Kurimoto et al. | 562/532 |
| 5,670,702 A | 9/1997 | Jackson et al. | 560/208 |
| 5,681,790 A | 10/1997 | Kim et al. | 502/164 |
| 5,684,188 A | 11/1997 | Hefner et al. | 562/532 |
| 5,700,752 A | 12/1997 | Kurimoto et al. | 502/311 |
| 5,728,894 A | 3/1998 | Nagano et al. | 568/479 |
| 5,739,391 A | 4/1998 | Ruppel et al. | 562/532 |
| 5,817,865 A | 10/1998 | Machhammer et al. | 560/208 |
| 5,821,390 A | 10/1998 | Ruppel et al. | 568/470 |
| 5,856,259 A | 1/1999 | Watanabe et al. | 502/305 |
| 5,877,108 A | 3/1999 | Suresh et al. | 502/20 |
| 5,892,108 A | 4/1999 | Shiotani et al. | 562/532 |
| 5,929,275 A | 7/1999 | Wada et al. | 562/545 |
| 5,948,683 A | 9/1999 | Koermer et al. | 436/37 |
| 5,948,726 A | 9/1999 | Moskovitz et al. | |
| 5,981,804 A | 11/1999 | Kurimoto et al. | 568/479 |
| 5,990,348 A | 11/1999 | Lyon et al. | 562/549 |
| 6,028,220 A | 2/2000 | Wada et al. | 562/546 |
| 6,043,184 A | 3/2000 | Karmakar et al. | 502/208 |
| 6,060,419 A | 5/2000 | Wijesekera et al. | 502/208 |
| 6,069,271 A | 5/2000 | Tanimoto et al. | 562/545 |

(56) References Cited

U.S. PATENT DOCUMENTS

| | | |
|---|---|---|
| 6,171,571 B1 | 1/2001 | Bedard et al. .............. 423/594.7 |
| 6,383,973 B1 | 5/2002 | Kimura et al. |
| 6,946,422 B2 | 9/2005 | Stevenson et al. |
| 7,229,945 B2 | 6/2007 | Kauffman |
| 7,232,788 B2 | 6/2007 | Liang et al. |
| 7,361,791 B2 | 4/2008 | Liang et al. |
| 7,485,596 B2 | 2/2009 | Kauffman et al. |
| 7,494,952 B2 | 2/2009 | Kauffman et al. |
| 7,501,377 B2 | 3/2009 | Liang et al. |
| 7,649,111 B2 | 1/2010 | Liang et al. |
| 7,649,112 B2 | 1/2010 | Stevenson et al. |
| 7,732,367 B2 | 6/2010 | Stevenson et al. |
| 7,799,946 B2 | 9/2010 | Galloway |
| 7,851,397 B2 | 12/2010 | Liang et al. |
| 7,923,404 B2 | 4/2011 | Stevenson et al. |
| 7,999,133 B2 | 8/2011 | Stevenson et al. |
| 8,088,947 B2 | 1/2012 | Kurakami et al. |
| 8,481,448 B2 | 7/2013 | Liang et al. |
| 2004/0192973 A1 | 9/2004 | Liang et al. |
| 2011/0207600 A1 | 8/2011 | Kauffman et al. |

FOREIGN PATENT DOCUMENTS

| | | | |
|---|---|---|---|
| EP | 0 223 877 B1 | 6/1987 | ............... B01J 23/88 |
| EP | 0 267 556 B1 | 5/1988 | ............... B01J 23/88 |
| EP | 0 279 374 B1 | 8/1988 | ............... B01J 23/88 |
| EP | 0 456 837 A1 | 6/1991 | ................ B01J 8/06 |
| EP | 0 450 596 B1 | 10/1991 | ............... B01J 23/88 |
| EP | 0 460 932 B1 | 12/1991 | ............... B01J 23/88 |
| EP | 0 501 794 B1 | 9/1992 | ............. B01J 23/887 |
| EP | 0 523 727 B1 | 1/1993 | ............... B01J 23/88 |
| EP | 0 558 028 B1 | 9/1993 | ............... B01J 23/88 |
| EP | 0 563 025 A1 | 9/1993 | ............ B01J 23/881 |
| EP | 0 574 895 A1 | 12/1993 | ............... B01J 23/88 |
| EP | 0 630 879 A1 | 12/1994 | ............ B01J 23/887 |
| EP | 0 685 260 A2 | 12/1995 | ............ B01J 23/887 |
| EP | 0 767 161 A1 | 4/1997 | ............. C07C 45/35 |
| EP | 1930074 A1 | 6/2008 | |
| EP | 2179793 A1 | 4/2010 | |

OTHER PUBLICATIONS

PCT ISR, Apr. 11, 2013.

HIGH MOLYBDENUM MIXED METAL OXIDE CATALYSTS FOR THE PRODUCTION OF UNSATURATED ALDEHYDES FROM OLEFINS

BACKGROUND OF THE INVENTION

1. Field of the Invention

Embodiments of this invention relate to highly active catalysts including molybdenum-containing mixed metal oxides for the production of unsaturated aldehydes from olefins, such as methacrolein, by gas phase catalytic oxidation of isobutylene in the presence of air or another gas containing molecular oxygen.

More particularly, embodiments of this invention relate to highly active catalysts including molybdenum-containing mixed metal oxides for the production of unsaturated aldehydes from olefins, where the molybdenum-containing mixed metal include oxides of (1) molybdenum or molybdenum and tungsten, (2) trivalent metals, (3) divalent metals, (4) monovalent metals and, (5) optionally, other metals that are added as oxides during catalyst preparation. The mixed metal oxides are characterized by having an anion to cation molar (ACM) ratio of ≥1.06 and <2.0 and a divalent to trivalent metal molar ratio between 1.95 and 2.15. The resulting catalyst compositions show an increased relative catalytic activity of at least 2 times compared to mixed metal oxides not having an ACM ratio greater than 1.00 and less than 2.00, and a divalent to trivalent metal molar ratio between 1.95 and 2.15. In other embodiments, when the ingredients at the indicated ratios are combined with a binder such as a silica binder, then the relative catalytic activity is even higher. In other embodiments the ingredients at the indicated ratios are combined with a pore forming agent to produce a different pore distribution in the final catalyst.

2. Description of the Related Art

Many catalysts have been disclosed for use in the production of acrolein or methacrolein by catalytic vapor phase oxidation of propylene or isobutylene. U.S. Pat. No. 4,816,603 discloses a catalyst for production of methacrolein and methacrylic acid of the formula:

$$Mo_aW_bBi_cFe_dNi_eSb_fX_gY_hZ_iA_jO_k$$

where X is potassium, rubidium and/or cesium, Y is phosphorus, sulfur, silicon, selenium, germanium and/or boron, Z is zinc and/or lead, A is magnesium, cobalt, manganese and/or tin, a is 12, b is 0.001 to 2, c is 0.01 to 3, d is 0.01 to 8, e is 0.01 to 10, f is 0.01 to 5, g is 0.01 to 2, h is 0 to 5, I is 0.01 to 5, j is 0 to 10 and k is sufficient to satisfy the valences.

U.S. Pat. No. 4,511,671 discloses a catalyst for manufacturing methacrolein of the formula:

$$Mo_aW_bBi_cFe_dA_eB_fC_gD_hO_x$$

where A is at least one of nickel and/or cobalt; B is at least one of alkali metals, alkaline earth metals and/or thallium; C is at least one of phosphorus, tellurium, antimony, tin, cerium, lead, niobium, manganese and/or zinc; D is at least one of silicon, aluminum, zirconium, and/or titanium; a is 12, b is 0 to 10, c is 0.1 to 10, d is 0.1 to 20, e is 2 to 20, f is 0 to 10, g is 0 to 4, h is 0 to 30 and x is determined by the atomic valences.

U.S. Pat. No. 4,556,731 discloses a catalyst for production of methacrolein and methacrylic acid of the formula:

$$A_aB_bFe_cX_dM_eMo_{12}O_x$$

where A is an alkali metal, such as potassium, rubidium, cesium or mixtures thereof, thallium, silver or mixtures thereof, B is cobalt, nickel, zinc, cadmium, beryllium, calcium, strontium, barium, radium or mixtures thereof, X is bismuth, tellurium or mixtures thereof and M is (1) Cr+W, Ge+W, Mn+Sb, Cr+P, Ge+P, Cu+W, Cu+Sn, Mn+Cr, Pr+W, Ce+W, Sn+Mn, Mn+Ge or combinations thereof, (2) Cr, Sb, Ce, Pn, Ge, B, Sn, Cu or combinations thereof, or (3) Mg+P, Mg+Cu, Mg+Cr, Mg+Cr+W, Mg+W, Mg+Sn or combinations thereof, a is 0 to 5, b is 0 to 20, c is 0 to 20, d is 0 to 20, e is 0.01 to 12 and x satisfies the valence requirements.

U.S. Pat. No. 5,245,083 discloses a catalyst for preparing methacrolein of a mixture of composition (1) of the formula:

$$Mo_aBi_bFe_cX_dZ_fO_g$$

where X is Ni and/or Co, Z is at least one of W, Be, Mg, S, Ca, Sr, Ba, Te, Se, Ce, Ge, Mn, Zn, Cr, Ag, Sb, Pb, As, B, P, Nb, Cu, Cd, Sn, Al, Zr and Ti, a is 12 b is 0.1 to 10, c is 0 to 20, d is 0 to 20, f is 0 to 4 and g satisfies the valence requirement and composition (2) of the formula:

$$A_mMo_nO_p$$

where A is at least one of K, Rb and Cs, m is 2, n is 1 to 9 and p is 3n+1.

U.S. Pat. No. 5,138,100 discloses a catalyst for preparing methacrolein with a mixture of composition (1) of the formula:

$$Mo_aBi_bFe_cX_dY_eZ_fO_g$$

where X is at least one of Ni and Co, Y is at least one of K, Rb, Cs and Ti, Z is at least one of the elements belonging to Groups 2, 3, 4, 5, 6, 7, 11, 12, 13, 14, 15 and 16, specifically beryllium, magnesium, calcium, strontium, barium, titanium, zirconium, cerium, niobium, chromium, tungsten, manganese, copper, silver, zinc, cadmium, boron, aluminum, germanium, tin, lead, phosphorus, arsenic, antimony, sulfur, selenium and tellurium, a is 12, b is 0.1 to 10, c is 0 to 20, d is 0 to 20, e is 0 to 2, f is 0 to 4, and g satisfies the valence requirement and composition (2) of the formula:

$$Ln_hMo_iO_j$$

where Ln is at least one of the rare earth elements, h is 0.2 to 1.5, I is 1 and j satisfies the valence requirement. The atomic ratio of the rare earth element to molybdenum is disclosed to be in the range from 0.2 to 1.5 with an atomic ratio less than 0.2 resulting in high selectivity but poor activity and with an atomic ratio greater than 1.5 resulting in high activity but poor selectivity.

U.S. Pat. No. 4,537,874 discloses a catalyst for production of unsaturated aldehydes of the formula:

$$Bi_aW_bFe_cMo_dA_eB_fC_gD_hO_x$$

where A is nickel and/or cobalt, B is at least one of alkali metal, alkaline earth metals and thallium, C is at least one of phosphorus, arsenic, boron, antimony, tin, cerium, lead and niobium, D is at least one of silicon, aluminum, zirconium and titanium, a is 0.1 to 10.0, b is 0.5 to 10.0, c is 0.1 to 10.0, d is 12, e is 2.0 to 20.0, f is 0.001 to 10.0, g is 0 to 10.0 and h satisfies the valence requirement. The ratio of a/b is 0.01 to 6.0 so that bismuth is combined very stably with tungsten and compounds such as bismuth trioxide and bismuth molybdate are not formed.

U.S. Pat. No. 5,728,894 discloses a catalyst for producing methacrolein of the formula:

$$Mo_{12}Bi_aCe_bK_cFe_dA_eB_fO_g$$

where A is Co or a mixture of Co and Mg having an atomic ratio of Mg to Co not more than 0.7, B is Rb, Cs or a mixture thereof, a is 0 to 8, b is 0 to 8, c is 0 to 1.2, d is 0 to 2.5, e is 1.0 to 12, f is 0 to 2.0, g satisfies the valence requirement. The relative atomic ratio of iron to bismuth and cerium should be $0<d/(a+b+d)\leq0.9$. The relative atomic ratio of bismuth, cerium and potassium should be $0.05\leq b/(a+b+c)\leq0.7$. The relative atomic ratio of potassium to bismuth and cerium should be $0<c/(a+b+c)\leq0.4$. Bismuth, cerium, potassium, iron and cobalt are indispensable elements for the disclosed invention.

U.S. Pat. No. 5,166,119 discloses a method for preparing a catalyst of molybdenum, bismuth, iron and cesium or thallium for producing methacrolein and methacrylic acid by gas phase catalytic oxidation of isobutylene or tert-butanol with molecular oxygen. There is no preference disclosed of cesium over thallium.

U.S. Pat. No. 6,946,422 discloses a process for making a catalyst containing oxides of molybdenum, bismuth, iron, cesium and, optionally, other metals, such as tungsten, cobalt, nickel, antimony, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium wherein metal compounds are dissolved and then precipitated as a catalyst precursor which is calcined to form a mixed metal oxide catalyst. The process of the present invention uses an organic acid, such as acetic acid, instead of nitric acid to dissolve the bismuth compound and, optionally, other metal compounds. The catalyst synthesized by this process may be used for the production of unsaturated aldehydes, such as methacrolein, by gas phase catalytic oxidation of olefins, such as isobutylene.

U.S. Pat. No. 7,229,945 disclosed a process for making a catalyst for production of unsaturated aldehydes, such as methacrolein, by gas phase catalytic oxidation of olefins, such as isobutylene, said catalyst containing oxides of molybdenum, bismuth, iron, cesium, tungsten, cobalt, nickel, antimony, magnesium and zinc. The process is a two-part synthesis of the catalyst with the water insoluble components in one part and the water soluble components in the other part. The water insoluble components are co-precipitated to form an intermediate catalyst precursor of a precipitated support incorporating oxides of the metal components. The intermediate catalyst precursor is filtered and washed to remove nitrates. The intermediate catalyst precursor is slurried with the remaining water soluble components. A final catalyst precursor is formed by removing the water and incorporating the water soluble components. This two-part process reduces the amount of nitrates in the final catalyst precursor.

U.S. Pat. No. 7,232,788 disclosed a catalyst for production of unsaturated aldehydes, such as methacrolein, by gas phase catalytic oxidation of olefins, such as isobutylene, contains oxides of molybdenum, bismuth, iron, cesium and, optionally, other metals. The catalyst has a certain relative amount ratio of cesium to bismuth, a certain relative amount ratio of iron to bismuth and a certain relative amount ratio of bismuth, iron, cesium and certain other metals to molybdenum and, optionally, tungsten. For a catalyst of the formula:

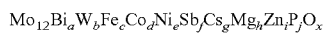

$$Mo_{12}Bi_aW_bFe_cCo_dNi_eSb_fCs_gMg_hZn_iP_jO_x$$

wherein a is 0.1 to 1.5, b is 0 to 4, c is 0.2 to 5.0, d is 0 to 9, e is 0 to 9, f is 0 to 2.0, g is from 0.4 to 1.5, h is 0 to 1.5, I is 0 to 2.0, j is 0 to 0.5 and x is determined by the valences of the other components, $c:g=3.3\text{–}5.0$, $c:a=2.0\text{–}6.0$ and $(3a+3c+2d+2e+g+2h+2i)/(2\times12+2b)=0.95\text{–}1.10$.

U.S. Pat. No. 7,361,791 disclosed a catalyst for production of unsaturated aldehydes, such as methacrolein, by gas phase catalytic oxidation of olefins, such as isobutylene, contains oxides of molybdenum, bismuth, iron, cesium and, optionally, other metals. The catalyst has a certain relative amount ratio of cesium to bismuth, a certain relative amount ratio of iron to bismuth and a certain relative amount ratio of bismuth, iron, cesium and certain other metals to molybdenum and, optionally, tungsten. For a catalyst of the formula:

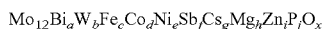

$$Mo_{12}Bi_aW_bFe_cCo_dNi_eSb_fCs_gMg_hZn_iP_jO_x$$

wherein a is 0.1 to 1.5, b is 0 to 4, c is 0.2 to 5.0, d is 0 to 9, e is 0 to 9, f is 0 to 2.0, g is from 0.4 to 1.5, h is 0 to 1.5, I is 0 to 2.0, j is 0 to 0.5 and x is determined by the valences of the other components, $c:g=3.3\text{-}5.0$, $c:a=2.0\text{-}6.0$ and $(3a+3c+2d+2e+g+2h+2i)/(2\times12+2b)=0.95\text{-}1.10$.

U.S. Pat. No. 7,494,952 disclosed a process for making a catalyst for production of unsaturated aldehydes, such as methacrolein, by gas phase catalytic oxidation of olefins, such as isobutylene, said catalyst containing oxides of molybdenum, bismuth, iron, cesium, tungsten, cobalt, nickel, antimony, magnesium and zinc. The process is a synthesis of the catalyst with aging or digestion of the reaction slurry with little or no agitation. A catalyst precursor is formed from the water insoluble and water soluble components and is dried. The metal oxide catalyst is formed by calcination of the catalyst precursor.

U.S. Pat. No. 7,501,377 disclosed a catalyst for production of unsaturated aldehydes, such as methacrolein, by gas phase catalytic oxidation of olefins, such as isobutylene, contains oxides of molybdenum, bismuth, iron, cesium and, optionally, other metals. The catalyst has a certain relative amount ratio of cesium to bismuth, a certain relative amount ratio of iron to bismuth and a certain relative amount ratio of bismuth, iron, cesium and certain other metals to molybdenum and, optionally, tungsten. For a catalyst of the formula:

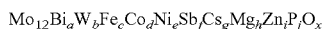

$$Mo_{12}Bi_aW_bFe_cCo_dNi_eSb_fCs_gMg_hZn_iP_jO_x$$

wherein a is 0.1 to 1.5, b is 0 to 4, c is 0.2 to 5.0, d is 0 to 9, e is 0 to 9, f is 0 to 2.0, g is from 0.4 to 1.5, h is 0 to 1.5, I is 0 to 2.0, j is 0 to 0.5 and x is determined by the valences of the other components, $c:g=3.3\text{-}5.0$, $c:a=2.0\text{-}6.0$ and $(3a+3c+2d+2e+g+2h+2i)/(2\times12+2b)=0.95\text{-}1.10$.

The prior art disclosed mixed metal oxide catalysts, which contain molybdenum, bismuth, iron, nickel, cobalt, cesium and other metals for the production of methacrolein. Furthermore, the prior art disclosed certain ranges of amounts of these metals. Some of the prior art disclosed relative ratios of certain components to other components. The effect of the selection of certain components for a mixed metal oxide catalyst compositions for the production of methacrolein and the relative relationship of some of these components to other components has not been investigated in complete detail. However, there is still an need in the art for mixed metal oxidation catalyst compositions, for the production of unsaturated aldehydes, having enhanced relative catalytic activity due to the addition of an amount of molybdenum above an anion to cation molar ratio of 1.0, where the amount is sufficient to ensure that all or substantially all divalent metals are converted to molybdate phases, where the increased molybdate-divalent metal oxide phases correlate with enhanced relative catalytic activity of the catalyst compositions of this invention compared to catalyst compositions not including the additional molybdenum.

SUMMARY OF THE INVENTION

Embodiments of this invention provide highly active catalysts for the production of unsaturated aldehydes and acids from olefins comprising mixed metal oxides including: (1) molybdenum or molybdenum and tungsten; (2) trivalent metals, M, selected from the group consisting of trivalent transition metals, trivalent non-transition metals, and mixtures thereof; (3) divalent metals, M', selected from the group consisting of alkaline earth metals, divalent transition metals, divalent non-transition metals, and mixtures thereof; and (4) monovalent metals, M", selected from the group consisting of alkali metals, monovalent transition metals, and mixtures thereof, wherein the mixed metal oxides have an anion to cation molar (ACM) ratio greater than 1.00 and less than 2.00; and an M' to M molar ratio between 1.95 and 2.15. The ACM ratio is defined as (2×([Mo]+[W]))/(3×[M]+2×[M']+[M"]).

Embodiments of this invention provide highly active molybdenum mixed metal oxide catalyst compositions including at least one compound of the general formula:

$$Mo_a W_b M_c M'_d M''_e Z_f O_g \quad (I)$$

where:
M is a trivalent metal (M) selected from the group consisting of trivalent transition metals, trivalent non-transition metals, and mixtures thereof;
M' is a divalent metal (M') selected from the group consisting of alkaline earth metals, divalent transition metals, divalent non-transition metals, and mixtures thereof;
M" is a monovalent (M") metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.0 and 0.4;
c is a number between 2.0 and 4.0;
d is a number between 5.0 and 8.0;
e is a number between 0.5 and 1.5;
f is a number between 0.5 and 1.5; and
g is a number that completes the valency of the formula;
wherein the mixed metal oxide has:
Mo is present in an amount sufficient to produce an anion to cation molar (ACM) ratio greater than 1.00 and less than 2.00; and
an M' to M molar ratio is between 1.95 and 2.15, and
wherein:
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3c+2d+e)$.

Other embodiments of the catalyst include those of formula (II), formula (III), formula (IV), formula (V), and formula (VI), as further described herein. Other aspects of the invention include processes for catalytic oxidation of olefins to aldehydes using the catalyst of any of the formulas described, as further described herein. Other aspects of the invention include the mixed metal oxides of any of formula (I), formula (II), formula (III), formula (IV), formula (V), and formula (VI). In each of the embodiments of catalysts, processes, and mixed metal oxides disclosed herein, the ACM ratio not only includes the broad range of greater than 1.00 and less than 2.00 as discussed above, but each of said embodiments also include, for said ACM ratio: the more preferred range of greater than 1.00 and less than 1.80, the even more preferred range of greater than 1.00 and less than 1.60, the even more preferred range of greater than 1.00 and less than 1.40, the even more preferred range of greater than 1.00 and less than 1.20, and the most preferred range of greater than or equal to 1.06 and less than 1.20. Additionally, each such embodiment includes the ACM ratio range of greater than or equal to 1.06 and less than 2.00; greater than or equal to 1.06 and less than 1.80; greater than or equal to 1.06 and less than 1.60; and, greater than or equal to 1.06 and less than 1.40.

The ranges recited above for ACM ratio and the M' to M molar ratio result in enhanced catalytic activity. In certain embodiments, the increased relative catalytic activity is at least 1.5 times the relative catalytic activity of the analogous catalyst not within the recited ranges. In other embodiments, the increased relative catalytic activity is at least 1.75 times a relative catalytic activity of the analogous catalyst not within the recited ranges. In other embodiments, the increased relative catalytic activity is at least 2.0 times a relative catalytic activity of the analogous catalyst not within the recited ranges. In other embodiments, the increased relative catalytic activity is at least 2.1 times a relative catalytic activity of the analogous catalyst not within the recited ranges. In other embodiments, the increased relative catalytic activity is at least 2.2 times a relative catalytic activity of the analogous catalyst not within the recited ranges. In other embodiments, the increased relative catalytic activity is at least 2.3 times a relative catalytic activity of the analogous catalyst not within the recited ranges. In other embodiments, the increased relative catalytic activity is at least 2.4 times a relative catalytic activity of the analogous catalyst not within the recited ranges. In other embodiments, the increased relative catalytic activity is at least 2.5 times a relative catalytic activity of the analogous catalyst not within the recited ranges.

For each of the embodiments of catalysts, processes, and mixed metal oxides disclosed herein, as applied to any and all of the formulas disclosed herein (including any one of formulas (I)-(VI)), the M' to M molar ratio not only includes the broad range of between 1.95 and 2.15 as discussed above, but each of said embodiments also include, for said M' to M molar ratio: the more preferred M' to M molar ratio of between 2.00 and 2.10, the more preferred M' to M molar ratio of between 2.05 and 2.10, the more preferred M' to M molar ratio of between 2.05 and 2.07, and the most preferred M' to M molar ratio of 2.06.

In the catalyst compositions of this invention, the molybdenum is present completely or substantially completely as molybdate, $MoO_4^{2-}$, which along with tungsten, if present, in the form of tungstate, $WO_4^{2-}$, represent the anions in determining the ACM ratio. The catalyst compositions of this invention are prepared using a total number of moles of molybdate, $[MoO_4^{2-}]_{total}$. The term substantially means that 90% of the molybdenum is in the form of molybdate, preferably, at least 95%, and especially, at least 99%. During catalyst preparation, a portion of $[MoO_4^{2-}]_{total}$ reacts with all or substantially all of the monovalent metals M" and trivalent metals M in the catalyst compositions, where substantially has an analogous meaning here. The number of moles of molybdate remaining are referred to as the net number of moles of molybdate, $[MoO_4^{2-}]_{net}$. The net number of moles of molybdate represents the moles of molybdate needed to react with the divalent metals, M'. The total number of moles of molybdate also includes an additional number of moles of molybdate referred to as the residual number of moles of molybdate, $[MoO_4^{2-}]_{res}$.

While not intended to being bound by any particular theory, we believe that the residual number of moles of molybdate ensures that all or substantially all the divalent metals M' are converted into M'-molybdate mixed metal oxides, resulting in an increased amount of these M'-molybdate mixed metal oxides in the catalyst compositions. We further believe that the increase in these M'-molybdate mixed metal oxides results in the increased relative catalytic activity of the catalyst compositions of this invention. Moreover, the inventors have found that a narrow range of $[MoO_4^{2-}]_{res}$ values increases the relative catalytic activity of the catalyst compositions of this invention, while values above and below this range decreases relative catalytic activity. Ideally, the residual number of moles of molybdate ranges from greater than or equal to 0.4 to less than 2.0. The term substantially relating to the conversion of M' metals means that at least 51% of the M' metals are reacted with molybdate to from M'-molybdenum mixed metal oxides, preferably, at least 75%, particularly, at least 85%, more particularly, at least 95%, and especially, at least 99%.

These compositional characteristics of the catalyst compositions of this invention may be expressed symbolically as well. Thus, the net number of moles of molybdate may be defined as $$[MoO_4^{2-}]_{net} = [MoO_4^{2-}]_{total} - ([M'] + [M''])$$

and the residual number of moles of molybdate may be defined as $$[MoO_4^{2-}]_{res} = [MoO_4^{2-}]_{net} - [M'].$$

The catalyst compositions of this inventions are characterized in that $[MoO_4^{2-}]_{res}$ is greater than or equal to 0.4 and less than 2.0. In other embodiments, $[MoO_4^{2-}]_{res}$ is between 0.5 and 1.5. In other embodiments, $[MoO_4^{2-}]_{res}$ is between 0.75 and 1.25. In other embodiments, $[MoO_4^{2-}]_{res}$ is between 0.8 and 1.0. In other embodiments, $[MoO_4^{2-}]_{res}$ is 0.9. It should be recognized that [Mo] is equal to $[MoO_4^{2-}]$ so that these symbolic representations set forth above may be formulated equally well in terms of [Mo].

Alternatively, the catalyst compositions of this invention may be characterized as comprising mixed metal oxides satisfying the following two conditions: (1) an ACM ratio greater than 1.00 and less than 2.00 and (2) an M' to M molar ratio between 1.95 and 2.15. In other embodiments, catalyst compositions of this invention may be characterized as comprising mixed metal oxides satisfying the following two conditions: (1) an ACM ratio greater than 1.00 and less than 1.80 and (2) an M' to M molar ratio between 1.95 and 2.15. In other embodiments, catalyst compositions of this invention may be characterized as comprising mixed metal oxides satisfying the following two conditions: (1) an ACM ratio greater than 1.00 and less than 1.60 and (2) an M' to M molar ratio between 1.95 and 2.15. In other embodiments, catalyst compositions of this invention may be characterized as comprising mixed metal oxides satisfying the following two conditions: (1) an ACM ratio greater than 1.00 and less than 1.40 and (2) an M' to M molar ratio between 1.95 and 2.15. In other embodiments, catalyst compositions of this invention may be characterized as comprising mixed metal oxides satisfying the following two conditions: (1) an ACM ratio greater than 1.00 and less than 1.20 and (2) an M' to M molar ratio between 1.95 and 2.15. In other embodiments, catalyst compositions of this invention may be characterized as comprising mixed metal oxides satisfying the following two conditions: (1) an ACM ratio greater than or equal to 1.06 and less than 1.20 and (2) an M' to M molar ratio between 1.95 and 2.15. The ACM ratios and M' and M molar ratios set forth above apply equally well to all mixed metal oxide of formulas (I-VI).

The fact that catalyst compositions prepared having this additional amount of molybdenum and satisfying these two conditions, correlated with unusually high relative catalytic activities compared to catalyst compositions not including the additional amount of molybdenum and satisfying these two conditions was wholly unexpected. It is known that catalyst compositions having a molar ratio of anions to cations of 1.0 (i.e., an equal molar ratio of metal anions to metal cations=1.0) have good catalyst performance. Here, we have found that catalyst compositions having an ACM ratio less than 1.0 had diminished relative catalytic activity and selectivity, and similarly, catalyst compositions having an ACM ratio 2.0 also had diminished relative catalytic activity and selectivity. However, when the ACM ratio is greater than or equal to 1.06, but less than 2.0 (1.06≤ACM ratio<2.0), then relative catalytic activity is increased dramatically, by as much as 2 to 2.5 times the relative catalytic activity of catalyst compositions not satisfying these two conditions. While not wanting to be bound to a particular theory, the inventors believe that the net and residual number of moles of molybdate result in the conversion of all or substantially all divalent metals, M', into molybdate-divalent mixed metal oxide phases and an increase in the amount of these mixed metal oxide phases in the final catalyst compositions, which results in the unexpected high relative catalytic activity of the catalyst compositions of this invention. We have also found that when the ingredients at the indicated ratios are combined with a binder such as a silica binder, then the relative catalytic activity may be even higher. We have further found that when the ingredients at the indicated ratios are combined with a pore forming agent or agents, catalyst compositions having different pore distributions in the final catalyst compositions may be prepared.

The processes of using the catalyst compositions of this invention are generally in a gas phase catalytic oxidation of an olefin to an aldehyde. For example, propylene or isobutylene may be oxidized with a molecular oxygen-containing gas in the presence of a catalyst compositions of the present invention to form a product stream including an aldehyde and an acid such as the unsaturated aldehydes acrolein or methacrolein and the unsaturated acids acrylic acid or methacrylic acid. In certain embodiments, the use of the catalyst compositions of the present invention is in a process to increase relative catalytic activity to the production of methacrolein and methacrylic acid.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
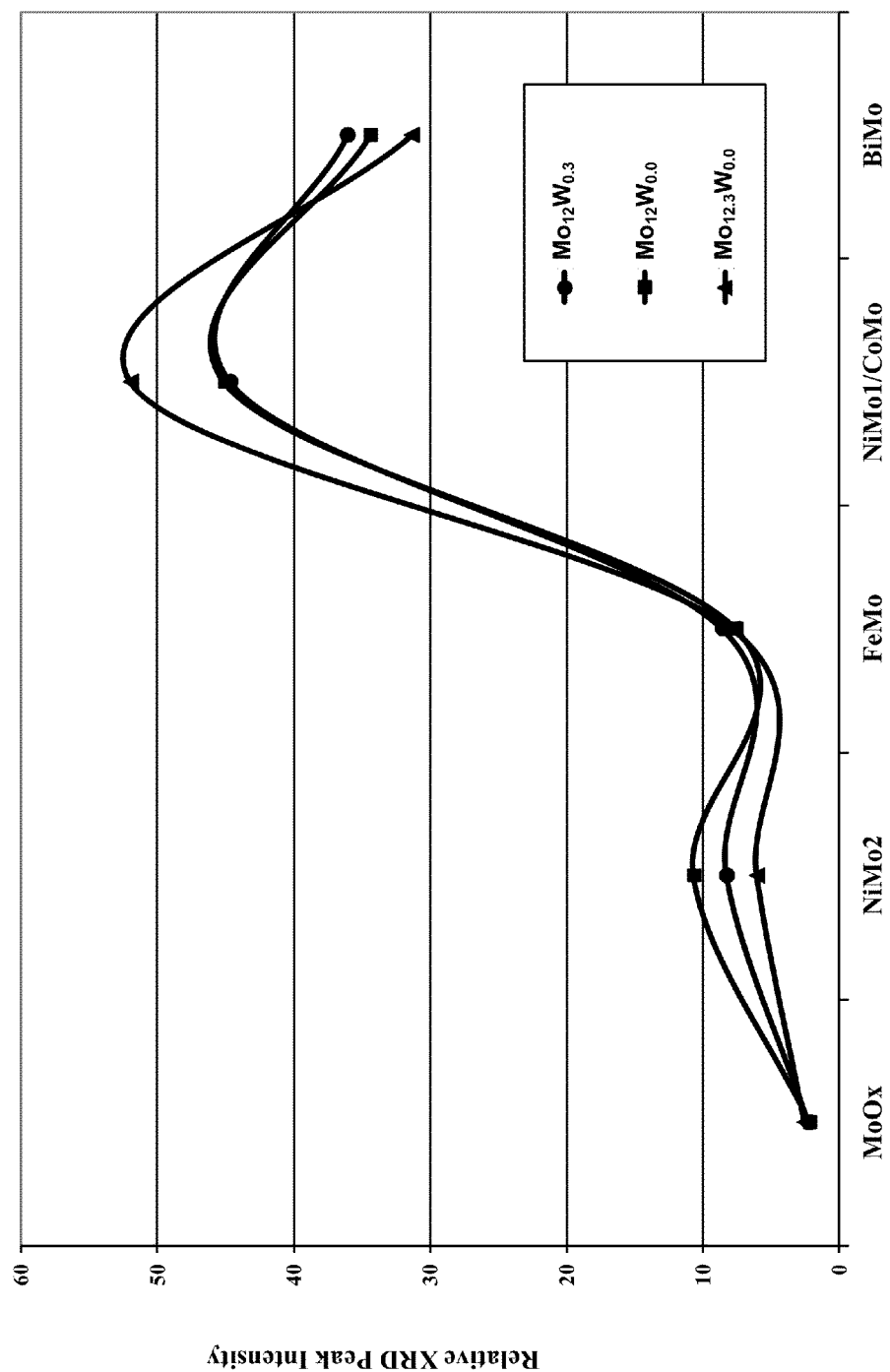
FIG. 1 depicts XDR peak intensities of three catalysts: a $Mo_{12}W_{0.3}$ catalyst, a $Mo_{12}W_{0.0}$ catalyst and a $Mo_{12.3}W_{0.0}$ catalyst, showing different oxide peak intensities including the intensity of the $NiMoO_4$ (phase1)/$CoMoO_4$ (NiMo1/CoMo) mixed oxide phase peaks.

According to the present invention, catalysts are provided for producing acrolein or methacrolein by oxidation of propylene or isobutylene. The oxidation is a catalytic reaction that converts an olefin in the presence of molecular oxygen to an unsaturated aldehyde and water:

$$H_2C=C(R)-CH_3+O_2 \rightarrow H_2C=C(R)-CHO+H_2O \qquad (5)$$

where R is hydrogen or a carbyl group. Carboxylic acids are also produced in a side reaction.

In all of the formulas described and set forth herein, we will use standard periodic table symbols for all elements such as molybdenum Mo, tungsten W, and oxygen O, all other terms such as M, M' and M" will be defined in the description of the formulas.

The catalysts of this invention are mixed metal oxides of the genera formula (I):

$$Mo_a W_b M_c M'_d M''_e Z_f O_g \qquad (I)$$

where:
  M is a trivalent metal selected from the group consisting of trivalent transition metals, trivalent non-transition metals and mixtures thereof;
  M' is a divalent metal selected from the group consisting of alkaline earth metals, divalent transition metals, divalent non-transition metals, and mixtures thereof;
  M" is a monovalent metal selected from the group consisting of alkali metals, monovalent transition metals, and mixtures thereof;
  Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
  a is a number between 12.3 and 14.0;
  b is a number between 0.0 and 0.4;
  c is a number between 2.0 and 4.0;
  d is a number between 5.0 and 8.0;
  e is a number between 0.5 and 1.5;
  f is a number between 0.5 and 1.5; and
  g is a number that completes the valency of the formula, wherein the mixed metal oxide has:
    Mo is present in an amount sufficient to produce an anion to cation molar (ACM) ratio greater than 1.00 and less than 2.00; and
    an M' to M molar ratio is between 1.95 and 2.15, and wherein
      the ACM ratio is defined as (2×[Mo]+2×[W]) to (3×[M]+2×[M']+[M"]) or (2×[Mo]+2×[W])/(3×[M]+2×[M']+[M"]) or 2(a+b)/(3c+2d+e).

The increased relative catalytic activity of the catalyst compositions of this invention was totally unexpected. The catalyst compositions of this invention, having an ACM ratio of at least 1.06 but less than 2.0 (1.06≤ACM ratio<2.0) and an M' to M molar ratio between 1.95 and 2.15, have dramatically increased relative catalytic activities. In fact, in certain embodiments, the increase in relative catalytic activity may be as much as 2.0 times that of catalyst compositions having the same metal components, but having ACM ratios outside of the range of less than or equal to 1.06 and less than 2.0 and an M' to M molar ratio outside of range of 1.95 to 2.15. In other embodiments, especially in the presence of binders, the increase in relative catalytic activity may be as much as 2.5 times.

In an embodiment of the present invention, the catalyst is of the general formula (II):

$$Mo_a W_b Bi_{c1} Fe_{c2} M_{c3} M'_d M''_e Z_f O_g \qquad (II)$$

where:
  M is a trivalent metal selected from the group consisting of trivalent transition metals, trivalent non-transition metals and mixtures thereof;
  M' is a divalent metal selected from the group consisting of alkaline earth metals, divalent transition metals, divalent non-transition metals, and or mixtures thereof;
  M" is a monovalent metal selected from the group consisting of alkali metals, monovalent transition metals, and mixtures thereof;
  Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
  a is a number between 12.3 and 14.0;
  b is a number between 0.2 and 0.4;
  c1, c2 and c3 sum to a number between 2.0 and 4.0;
  d is a number between 5.0 and 8.0;
  e is a number between 0.5 and 1.5;
  f is a number between 0.5 and 1.5; and
  g is a number that completes the valency of the formula, wherein Bi and Fe in formula (II) are in their plus three oxidation states,
wherein the mixed metal oxide has:
  Mo is present in an amount sufficient to produce an anion to cation molar (ACM) ratio greater than 1.00 and less than 2.00; and
  an M' to M molar ratio is between 1.95 and 2.15; and
wherein
  the ACM ratio is defined as (2×[Mo]+2×[W]) to (3×[M]+2×[M']+[M"]) or (2×[Mo]+2×[W])/(3×[M]+2×[M']+[M"]) or 2(a+b)/(3(c1+c2+c3)+2d+e).

The catalyst compositions of this invention may also include 1 to 20 wt. % of a silica binder such as LUDOX®-40 and 0.1 to 5 wt. % of a pore former such as a polyethylene glycol (PEG), where the wt. % is based on the total weight of the catalyst.

In another embodiment of the invention the catalyst is of the formula (III):

$$Mo_a W_b Bi_{c1} Fe_{c2} M_{c3} Ni_{d1} Co_{d2} M'_{d3} M''_e Z_f O_g \qquad (III)$$

where:
  M is a trivalent metal selected from the group consisting of trivalent transition metals, trivalent non-transition metals and mixtures thereof;
  M' is a divalent metal selected from the group consisting of alkaline earth metals, divalent transition metals, divalent non-transition metals, and mixtures thereof;
  M" is a monovalent metal selected from the group consisting of alkali metals, monovalent transition metals, and mixtures thereof;
  Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
  a is a number between 12.3 and 14.0;
  b is a number between 0.2 and 0.4;
  c1, c2 and c3 sum to a number between 2.0 and 4.0;
  d1, d2 and d3 sum to a number between 5.0 and 8.0;
  e is a number between 0.5 and 1.5;
  f is a number between 0.5 and 1.5; and
  g is a number that completes the valency of the formula, wherein Bi and Fe in formula (III) are in their plus three oxidation states and Ni and Co in formula (III) are in their plus two oxidation states, wherein the mixed metal oxide has:
Mo is present in an amount sufficient to produce an anion to cation molar (ACM) ratio greater than 1.00 and less than 2.00; and
an M' to M molar ratio is between 1.95 and 2.15, and wherein
the ACM ratio is defined as (2×[Mo]+2×[W]) to (3×[M]+2×[M']+[M"]) or (2×[Mo]+2×[W])/(3×[M]+2×[M']+[M"]) or 2(a+b)/(3(c1+c2+c3)+2(d1+d2+d3)+e).

The catalyst compositions of this invention may also include 1 to 20 wt. % of a silica binder such as LUDOX®-40 and 0.1 to 5 wt. % of a pore former such as a polyethylene glycol (PEG), where the wt. % is based on the total weight of the catalyst.

In another embodiment of the invention the catalyst is of the formula (IV):

$$Mo_aW_bBi_{c1}Fe_{c2}M_{c3}Ni_{d1}Co_{d2}Mg_{d3}M'_{d4}M''_eZ_fO_g \quad (IV)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2, d3 and d4 sum to a number between 5.0 and 8.0;
e is a number between 0.5 and 1.5;
f is a number between 0.5 and 1.5; and
g is a number that completes the valency of the formula, wherein Bi and Fe in formula (IV) are in their plus three oxidation states and Ni, Co, and Mg in formula (IV) are in their plus two oxidation states,
wherein the mixed metal oxide has:
Mo is present in an amount sufficient to produce an anion to cation molar (ACM) ratio greater than 1.00 and less than 2.00; and
an M' to M molar ratio is between 1.95 and 2.15, and wherein
the ACM ratio is defined as (2×[Mo]+2×[W]) to (3×[M]+2×[M']+[M"]) or (2×[Mo]+2×[W])/(3×[M]+2×[M']+[M"]) or 2(a+b)/(3(c1+c2+c3)+2(d1+d2+d3+d4)+e).

The catalyst compositions of this invention may also include 1 to 20 wt. % of a silica binder such as LUDOX®-40 and 0.1 to 5 wt. % of a pore former such as a polyethylene glycol (PEG), where the wt. % is based on the total weight of the catalyst.

In another embodiment of the invention the catalyst is of the formula (V):

$$Mo_aW_bBi_{c1}Fe_{c2}M_{c3}Ni_{d1}Co_{d2}Mg_{d3}Zn_{d4}M'_{d5}Cs_{e1}M''_{e2}Z_fO_g \quad (V)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2, d3, d4, and d5 sum to a number between 5.0 and 8.0;
e1 and e2 sum to a number between 0.5 and 1.5;
f is a number between 0.5 and 1.5; and
g is a number that completes the valency of the formula, wherein Bi and Fe in formula (V) are in their plus three oxidation states, Ni, Co, Mg, and Zn in formula (V) are in their plus two oxidation states and Cs in formula (V) is in its plus one oxidation state,
wherein the mixed metal oxide has:
Mo is present in an amount sufficient to produce an anion to cation molar (ACM) ratio greater than 1.00 and less than 2.00; and
an M' to M molar ratio is between 1.95 and 2.15, and wherein
the ACM ratio is defined as (2×[Mo]+2×[W]) to (3×[M]+2×[M']+[M"]) or (2×[Mo]+2×[W])/(3×[M]+2×[M']+[M"]) or 2(a+b)/(3(c1+c2+c3)+2(d1+d2+d3+d4+d5)+(e1+e2)).

The catalyst compositions of this invention may also include 1 to 20 wt. % of a silica binder such as LUDOX®-40 and 0.1 to 5 wt. % of a pore former such as a polyethylene glycol (PEG), where the wt. % is based on the total weight of the catalyst.

In another embodiment of the invention the catalyst is of the formula (VI):

$$Mo_aW_bBi_{c1}Fe_{c2}M_{c3}Ni_{d1}Co_{d2}Mg_{d3}Zn_{d4}M'_{d5}Cs_{e1}M''_{e2}Sb_{f1}Z_{f2}O_g \quad (VI)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metal, and or mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2, d3, d4, and d5 sum to a number between 5.0 and 8.0;
e1 and e2 sum to a number between 0.5 and 1.5;
f1 and f2 sum to a number between 0.5 and 1.5; and
g is a number that completes the valency of the formula, wherein Bi and Fe in formula (VI) are in their plus three oxidation states, Ni, Co, Mg, and Zn in formula (VI) are in their plus two oxidation states and Cs in formula (VI) is in its plus one oxidation state, wherein the mixed metal oxide has:
  Mo is present in an amount sufficient to produce an anion to cation molar (ACM) ratio greater than 1.00 and less than 2.0; and
  an M' to M molar ratio is between 1.95 and 2.15, and wherein
    the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3(c1+c2+c3)+2(d1+d2+d3+d4+d5)+(e1+e2))$.

Although not intending to be bound by theory, it is believed that when the mixed metal oxide has a ACM ratio greater than 1.00 and less than 2.0, and a M' to M molar ratio between 1.95 and 2.15, all or substantially all of the M' metals are converted to M'-molybdates, increasing the concentration of Mo-M' oxide phases (molybdenum divalent metal oxide phases) in the mixed metal oxide. This results in a significant enhancement of catalytic activity, routinely showing an increase of catalytic activity of at least two times (i.e., at least a doubling of activity). This enhancement of catalytic activity is even more prominent in the preferred ranges of ACM ratio and M' to M molar ratio described herein.

The catalyst compositions of this invention may also include 1 to 20 wt. % of a silica binder such as LUDOX®-40 and 0.1 to 5 wt. % of a pore former such as a polyethylene glycol (PEG), where the wt. % is based on the total weight of the catalyst.

The process of making the catalyst is generally to dissolve the metal compounds in water or in an acid, precipitate a solid catalyst precursor to form a slurry, separate the solid by removing liquid from the slurry to leave a solid, dry the solid, and calcine the solid to form a mixed metal oxide catalyst. The Mo or Mo and W metal compounds are divalent anionic salts (e.g., ammonium $MoO_4^{2-}$ and ammonium $WO_4^{2-}$). The M metal compounds are cationic salts (e.g., nitrates, halides, organic acid, inorganic acid, hydroxides, carbonates, oxyhalides, sulfates and other groups which may exchange with oxygen under high temperatures so that the metal compounds become metal oxides, etc.). The M' metal compounds are divalent cationic salts (e.g., nitrates, halides, organic acid, inorganic acid, hydroxides, carbonates, oxyhalides, sulfates and other groups which may exchange with oxygen under high temperatures so that the metal compounds become metal oxides, etc.). The M" metal compounds are monovalent cationic salts (e.g., nitrates, halides, organic acid, inorganic acid, hydroxides, oxyhalides, sulfates and other groups which may exchange with oxygen under high temperatures so that the metal compounds become metal oxides, etc.). The Z compounds are either neutral oxides, other neutral compounds or compounds that do not enter into the anion to cation molar ratio. In one embodiment of the invention, the metal compounds are soluble in water or an acid. In another embodiment of the invention, the molybdenum compound and the tungsten compound are ammonium salts, such as ammonium paramolybdate or ammonium molybdate and ammonium paratungstate or ammonium tungstate, respectively, the M metals are nitrates such as bismuth nitrate and ferric nitrate, the M' metals are nitrates such as cobaltous nitrate, nickel nitrate, zinc nitrate, and magnesium nitrate, the M" metals are nitrates such as lithium nitrate, sodium nitrate, potassium nitrate, rubidium nitrate, and cesium nitrate, and Z is an element in the form of an oxide when added to a precatalyst preparation and is selected from the group consisting of cerium, antimony, phosphorus, boron, sulfur, silicon, aluminum, titanium, tellurium, vanadium, zirconium, niobium, and mixtures thereof. In one embodiment of the invention, the bismuth, iron, cesium, cobalt, nickel, magnesium and zinc compounds are nitrates. Of course, the M, M' and M" cationic metal salts are used in the calculation of the anion to cation molar ratio. The binders and pore formers may be added at any stage in the preparation method. In certain embodiments, the binders and pore formers may be added to the final slurry prior to drying.

The present invention does not depend on a particular order of addition of the components. While a particular order of addition of the various metal compound components may affect the performance of the catalyst, the present invention is directed toward the particular relative amount of certain components to other components without regard to the order in which the steps in the process of making the catalyst occur.

Suitable trivalent metals M include, without limitation, trivalent transition metals including Sc, Fe, Y, La, Ac, Nd, Pm, Gd, Dy, Ho, and Er, and non transition metal including Ga, In and Bi. Suitable divalent metals M' include, without limitation, alkaline earth metals including Be, Mg, Ca, Sr, and Ba, divalent transition metals including Co, Ni, Cu, Zn, Pd, Pt, Cd, and Hg and non-transition metals including Pb. Suitable monovalent metals M" include, without limitation, alkali metals including Li, Na, K, Rb, and Cs, and monovalent transition metals including Ag and Au. It should be understood that the above listed metals may also exist in other oxidation states, but in the mixed metal oxides of formulas (II-VI), the above listed metals have the specified valence. Thus, in the formulas, Bi and/or Fe are added as a trivalent salt and will exist in the final catalyst as trivalent oxides, similarly, Ni, Co, Mg, and/or Zn are added as a divalent salt and will exist in the final catalyst as divalent oxides.

An example of making the catalyst of the claimed invention is to dissolve an ammonium salt of molybdenum, such as ammonium paramolybdate or ammonium molybdate and/or an ammonium salt of tungsten, such as ammonium paratungstate or ammonium tungstate in water, dissolve a bismuth nitrate in an acid, dissolve an iron nitrate and, optionally, a cobalt nitrate, a nickel nitrate, a magnesium nitrate, and a zinc nitrate in water or in the acid with the bismuth nitrate, mix the solutions at a temperature in the range from 40° C. to 100° C., or at 60° C. to 95° C., to obtain a precipitate to form a slurry and then add a cesium nitrate and, optionally, an antimony oxide to the slurry while maintaining the temperature. The cesium nitrate and the antimony oxide may be added to the slurry as solids. The slurry may be aged for 2 to 24 hours, for 8 to 18 hours or for 5 to 10 hours. The liquid of the slurry is removed by evaporation and the solid precipitate is dried and calcined to obtain a catalyst. The liquid may be removed and the solid precipitate dried at the same time by spray drying. The liquid may be evaporated at a temperature of 50° C. to 125° C. The binders and pore formers may be added at any stage in the preparation method. In certain embodiments, the binders and pore formers may be added to the final slurry prior to drying.

Drying of the catalyst precursors may be in air or an inert gas and in an oven or a spray dryer. In one embodiment of the invention, drying is in an oven in air at a temperature of 100° C. to 150° C. for 2 to 5 hours.

One purpose of calcination of the catalyst precursor is to obtain an oxide of the metal components. The catalyst precursor may be calcined at a temperature of 200° C. to 600° C. for 1 to 12 hours. Calcination may be in two stages, one at a temperature of 150° C. to 400° C. for 1 to 5 hours and another at a temperature of 400° C. to 600° C. for 4 to 8 hours with a temperature ramp of 1-20° C./min, or of 5-10° C./min. In an embodiment of the invention for a two-stage calcination, the first is at a temperature of 290° C. to 310° C. for 2 hours and second at a temperature of 460° C. to 500° C. for 6 hours.

Denitrification may occur in the first step. In the alternative, calcination is in one stage by increasing the temperature from ambient temperature to about 485° C. over two hours instead of an initial step or denitrification. Calcination may be done in a high temperature oven or kiln.

The catalyst compositions may be processed by sieving, forming and other means known in the art to obtain catalyst particles of a certain size. Desired particle size and particle size distribution are related to the design of the reactor (size, shape, configuration, etc.), to the pressure drop intended for the process and to the process flow. For a two stage calcination, the catalyst may be sieved or formed after the first stage calcination and before the second stage calcination. In a commercial process the catalyst precursors may be sieved and formed after spray drying and before calcination.

Figure 2:
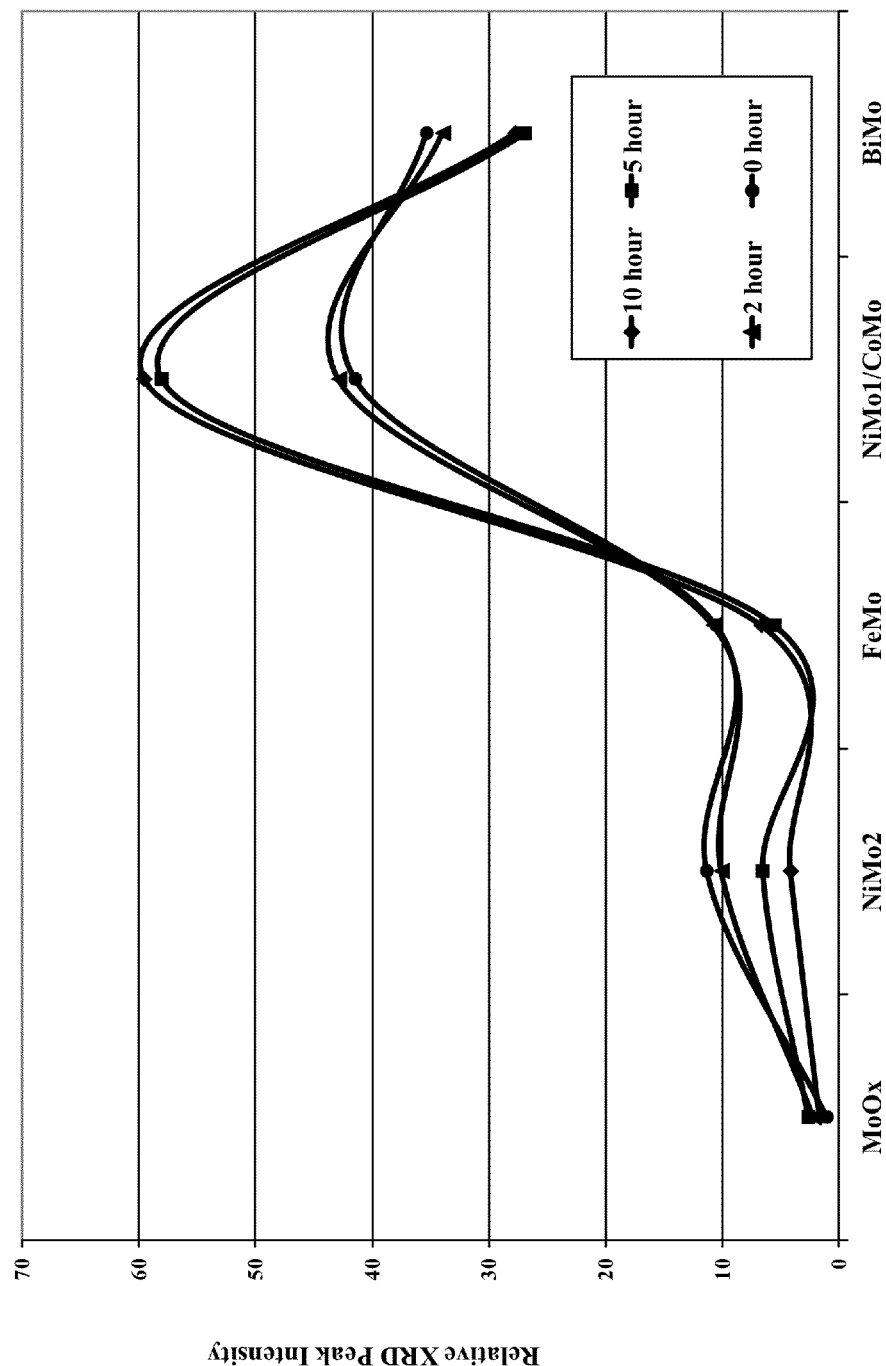
FIG. 2 depicts XRD peak intensities of a catalyst subjected to different digestion times, showing different oxide peak intensities including the intensity of $NiMoO_4$ (phase1)/$CoMoO_4$ (NiMo1/CoMo) mixed oxide phase peaks.
Figure 3:
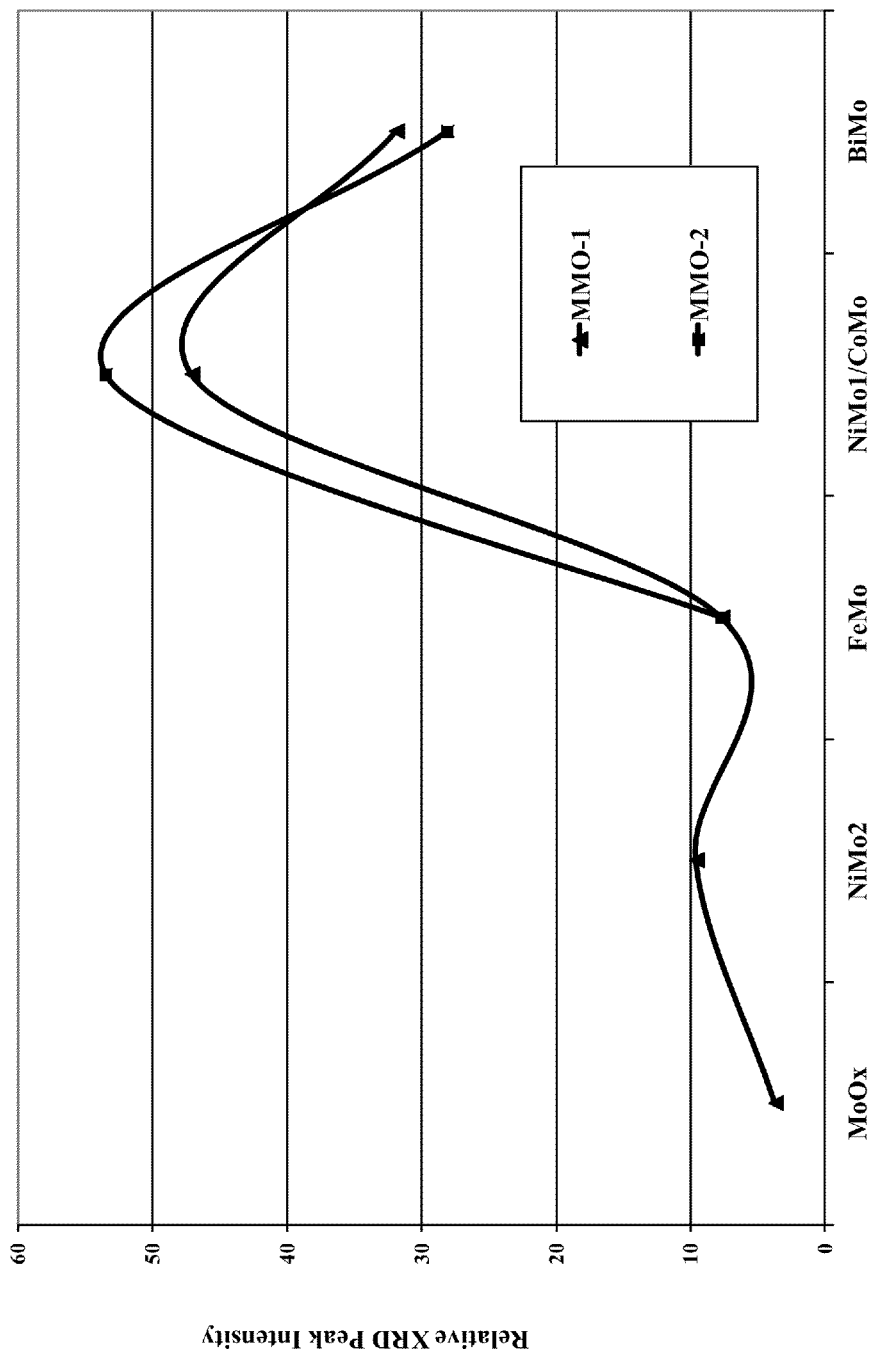
FIG. 3 depicts XRD peak intensities of a MMO-1 catalyst and a MMO-2 catalyst, showing different oxide peak intensities including the intensity of the $NiMoO_4$ (phase1)/$CoMoO_4$ (NiMo1/CoMo) phase peaks.

The conventional mixed metal oxide catalysts containing molybdenum are referred to as MMO-1 catalysts, and the mixed metal oxide catalyst compositions containing molybdenum of this invention are referred to as MMO-2 catalysts. When the term MMO is used, the term is referring to any mixed metal oxide catalyst including MMO-1, MMO-2 and any other mixed metal oxide catalysts used in aldehyde, such as methacrolein, production. The X-ray diffraction (XRD) pattern of the mixed metal oxide catalyst compositions made according to the present invention were measured. These catalyst compositions were found to have XRD patterns including diffraction peaks at diffraction angles of 2θ, measured using Cu Kα radiation, between 24 and 29 degrees. FIGS. 1-3 show XRD peak intensities for peaks corresponding to the various crystal phases of comparative MMO-1 catalysts, and MMO-2 catalysts of this invention. It is believed that MMO-1 and MMO-2 catalysts include peaks from left to right corresponding to a $MoO_x$ phase, a $NiMo_2$ phase 2 oxide, a FeMo oxide phase, a NiMo (phase 1)/CoMo mixed oxide phase (sometimes referred to herein as NiMo1/CoMo) and a BiMo oxide phase. There may be several additional diffraction peaks present in a catalyst composition of the present invention, but these peaks will normally be evident. It is also believed that the increased intensities of the highest XRD peaks correspond to increased amounts of the NiMo1/CoMo phase in the mixed metal oxides of this invention, where the increased amounts of the NiMo1/CoMo phase are believed to be primarily responsible for the increased relative catalytic activities of the catalyst compositions of this invention. FIG. 1 shows XRD data for three MMO-1 catalyst (appearing as $Mo_{12}W_{0.3}$, $Mo_{12}W_{0.0}$, and $Mo_{12.3}W_{0.0}$ in the legend). The significance of FIG. 1 is that the NiMo1/CoMo phase peak intensity is enhanced upon addition of Mo, but not enhanced upon the addition of W.

The catalyst of the present invention may be used as an unsupported catalyst or a supported catalyst. The surface area of an unsupported catalyst is from 0.1 to 150 m²/g or from 1 to 20 m²/g. If supported, the support should be an inert solid which is chemically unreactive with any of the active components of the catalyst and in one embodiment of the invention is silica, alumina, niobia, titania, zirconia or mixtures thereof. The catalyst may be affixed to the support by methods known in the art, including incipient wetness, slurried reactions and spray drying. The catalyst compositions, supported or unsupported, are not limited by shape, size or particle distribution and may be formed as appropriate for the reaction vessel in the process. Examples are powder, granules, spheres, cylinders, saddles, etc.

The catalysts compositions are used in the gas phase catalytic oxidation of a feedstock gas comprising an olefin, such as propylene or isobutylene, with a molecular oxygen-containing gas, such as oxygen, to produce an aldehyde, such as acrolein or methacrolein. Oxygen may be supplied in the pure form or in an oxygen-containing gas, such as air or as an oxygen-diluent gas mixture. The diluent gas may be nitrogen, a hydrocarbon which is gaseous under the process conditions or carbon dioxide. Water and/or an inert gas, such as nitrogen, may also be present. In one embodiment of the invention, the reaction temperature is from 250° C. to 450° C. or from 330° C. to 410° C. The reactor may be a fixed bed or a fluidized bed reactor. Reaction pressure may be from 0 to 100 psig or from 0 to 55 psig. Space velocity may be from 1000 to 12,500 hr$^{-1}$, 5000 to 10,000 hr$^{-1}$ or 7500 to 10,000 hr$^{-1}$. Operating conditions will depend upon the specifics of catalyst performance and the economics of process design for the individual process.

Suitable binder for use in the present invention include, without limitation, silica binders, alumina binder, kaoline binders, colloidal metal oxide binders, colloidal metalloid oxide binders or mixtures thereof. Exemplary colloidal metal oxide binders, colloidal metalloid oxide binders include, without limitation, silica-containing colloidal binders, alumina-containing colloidal binders, or mixtures thereof. Exemplary silica binders and alumina binders include, without limitation, LUDOX® colloidal silica catalyst binders, LUDOX® HS colloidal silica catalyst binders, and LUDOX® AS colloidal silica catalyst binders available from W.R. Grace & Co. such as LUDOX® HS-40 colloidal silica, NYACOL® colloidal alumina available from Nyacol Nano Technologies, Inc., binders disclosed in U.S. Pat. No. 5,948,726.

Suitable pore formers for use in this invention include, without limitation, formates, oxalates, citrates, acetates, amine complex salts, ammonium salts, organic molecule, organic particle, organic nano-particle or mixtures thereof, that convert to a gas during catalyst calcination. Exemplary pore formers include, without limitation, carboxylic acids, polyols, saccharides and polysaccharides, ammonium organic compounds, polyethylene glycols (PEGs), alcohols, amines, other organic compounds that undergo thermal decomposition to volatile components and mixtures thereof. Exemplary examples of such ammonium-containing compounds include, without limitation, ammonium salts of alkanoic (carboxylic) acids, or mixtures or combinations thereof.

The invention having been generally described, the following examples are given as particular embodiments of the invention and to demonstrate the practice and advantages thereof. It is understood that the examples are given by way of illustration and are not intended to limit the specification or the claims to follow in any manner.

Experiments of the Invention

The present invention affords unexpected improvements in mixed metal oxide catalysts for oxidation of olefins to unsaturated aldehydes such as the oxidation of isobutylene to methacrolein in the first stage of the MMA process. The improvement comprises a significant increase in relative catalytic activity of up to 2 and even up to 2.5 times due to a novel molar ratio of anions to cations and a novel divalent metal to trivalent metal molar ratio in the catalyst formulation compared to the conventional catalyst formulations. In certain embodiments, the improvement may be further improved with the addition of a binder such as a silica binder. In other embodiments, the catalyst preparation may be performed in the presence of an organic pore former. The conventional molybdenum-containing catalysts are referred to as MMO-1 catalysts, and the molybdenum-containing catalysts of this invention are referred to as MMO-2 catalysts, while MMO refers to all mixed metal oxide catalysts.

Definition of Anion to Cation Molar Ratio

The anion to cation molar (ACM) ratio is defined in Equation 1:

$$ACM\ ratio = \frac{2 \times ([Mo] + [W])}{3 \times [M] + 2 \times [M'] + 1 \times [M'']}$$

where [Mo] represents moles of Mo oxide anions, [W] represents moles of W oxide anions, [M] represents moles of trivalent metal cations, [M'] represents moles of divalent metal cations and [M''] represents moles of monovalent metal cations. Of course, the anions and cations are present during catalyst preparation, i.e., the charge on the metal sources is either negative (anions) or positive (cations). After preparation, the metal sources are converted to mixed metal oxides in the final catalyst. For example, an MMO-1 catalyst having the general formula:

$$Mo_{12}W_{0.3}Bi_{1.0}Fe_{2.4}Ni_{4.0}Co_{2.0}Mg_{0.5}Zn_{0.5}Cs_{0.6}Sb_{0.7}O_g$$

where g is a number that satisfies the valency of the catalyst. This MMO-1 catalyst has a near equivalency of anions and cations: ACM ratio=2×(12+0.3)/(3×(1.0+2.4)+2×(4.0+2.0+0.5+0.5)+0.6)=0.992≈1.0. Similarly, an MMO-2 catalyst having the general formula:

$$Mo_{12.9}W_{0.3}Bi_{1.0}Fe_{2.4}Ni_{4.0}Co_{2.0}Mg_{0.5}Zn_{0.5}Cs_{0.6}Sb_{0.7}O_g$$

where g is a number that satisfies the valency of the catalyst. This MMO-2 catalyst has a greater amount of anions to cations: ACM ratio=2×(12.9+0.3)/(3×(1.0+2.4)+2×(4.0+2.0+0.5+0.5)+0.6)=1.065≈1.1. All of the metal sources are salts (e.g., ammonium salts or nitrate salts) in the preparation and are considered to exist as anions or cations. Antimony is considered to have a neutral charge existing only as a neutral oxide. When calcined, the catalyst is considered to be charge neutral with the charges balanced by oxygen. When only the molybdenum is increased above the stoichiometric amount to give an ACM ratio greater than 1.00 and less than 2.00, then a relative catalytic activity increase is observed. The relative catalytic activity increase may be on the order of 2.0 to 2.5 times the relative catalytic activity of an analogous MMO-1 catalyst having an ACM ratio near 1.0. In certain embodiments, a binder is included in the catalyst, and the binder also acts to increase the relative catalytic activity. In certain embodiments, a binder and a pore former are included in the catalyst, and the binder and pore former also act to increase the relative catalytic activity.

Definition of Conversion and Selectivity

The activity of the catalyst compositions of this invention were defined relative to an internal reference catalyst. The internal reference catalyst has an activity defined as 1.0, so that if a catalyst shows an activity 30% higher than the internal reference catalyst, then this catalyst would have a relative catalytic activity or relative activity of 1.3. Similarly, the relative catalytic selectivity or relative selectivity of the internal reference catalyst is defined as 0.0. The selectivity vs. conversion curve is compared between a catalyst of this invention and the internal reference catalyst, so that if the catalyst of this invention showed a selectivity 1.0% higher than the internal reference catalyst at the same percentage conversion of methacrolein, then, that catalyst would have a relative selectivity of 1.0. The data set forth in the tables below are consistent within each table, but the data between tables are not directly comparable.

To understand the following results, the following definitions are set forth for actual conversion of a reactant and actual selectivity to a given product:

% conversion of $i\text{-}C_4H_8$={[moles of $i\text{-}C_4H_8$ converted)]/[(moles of unconverted $i\text{-}C_4H_8$+moles of $i\text{-}C_4H_8$ converted)]}*100

% selectivity to MAC={[(moles of MAC produced)]/[(moles of all products produced)]}*100

% selectivity to MAA={[(moles of MAA produced)]/[(moles of all products produced)]}*100 where $i\text{-}C_4H_8$ is isobutene, MAC is methacrolein MAA is methacrylic acid, and the moles of all products produced is on a four-carbon product count.

MMO-2 Catalyst Test Results

The reference, unbound laboratory catalyst sample that gave the best performance, the catalyst of Example 1 showed a relative catalytic activity of 2.1 with 84% selectivity at 96% conversion. However, as this sample is unbound, it would not be used commercially and, therefore, is not a good catalyst for comparative purposes to bound samples. A commercially available reference catalyst was, therefore, used for comparison purposes to bound samples. The Example 3 and Example 4 catalysts were prepared using this commercially available catalyst calcined using two different calcination procedures as reference catalysts to compare bound MMO-2 catalysts of this invention represented by the MMO-2 catalyst compositions of Example 7, Example 8 and Example 9.

In order to make a side-by-side comparison of the reference MMO-1 catalysts and the MMO-2 catalysts of this invention for the oxidation of isobutylene to methacrolein, we used polyethylene glycol (PEG) as a pore former and a LUDOX®-40 as a silica binder to make bound catalysts. All of the MMO-2 catalysts were prepared to have a nominal ACM ratio of about 1.1, i.e., an ACM greater than or equal to 1.06. Laboratory samples prepared according to this method show a 220% to 250% increase in relative catalytic activity, while maintaining good relative selectivity, preferably ±2%, as tabulated in Table 1.

TABLE 1

Improved MMO Catalyst Results

| Example | Sample Description | % $i\text{-}C_4H_8$ Conversion | % MAC + % MAA Selectivity† | Relative Activity | ACM Ratio |
|---------|-------------------|-------------------------------|---------------------------|-------------------|-----------|
| Unbound MMO-1 Catalyst | | | | | |
| 1 | particle: −20/+30 mesh | 96 | 84 | 2.1 | 1.00 |
| 2 | Slow ramp, long denitrification cycle. Catalyst obtained by filtering slurry. | na | na | 0.12 | 2.27 |

TABLE 1-continued

Improved MMO Catalyst Results

| Example | Sample Description | % i-$C_4H_8$ Conversion | % MAC + % MAA Selectivity[†] | Relative Activity | ACM Ratio |
|---------|-------------------|------------------------|------------------------------|-------------------|-----------|
| | Bound MMO-1 Catalyst | | | | |
| 3 | 25 kg commercially manufactured MMO-1, extrudate, 1/16" diameter, calcined in 4" calciner. | 96 | 81 | 2.1 | 1.00 |
| 4 | 25 kg commercially manufactured extrudate, 1/16" diameter, calcined in screen calciner. | 96 | 83 | 2.1 | 1.00 |
| | Unbound MMO-2 Catalyst | | | | |
| 5 | Slow ramp, long denitrification cycle. | 96 | 84 | 3.6 | 1.07 |
| | Unbound MMO-1 Catalyst | | | | |
| 6 | Slow ramp, long denitrification cycle. | 96 | 81 | 1.4 | 0.95 |
| | Bound MMO-2 Catalyst | | | | |
| 7 | LUDOX ®-40 silica binder + PEG pore former. Rapid ramp, short denitrification cycle. | 96 | 77 | 5.2 | 1.07 |
| 8 | LUDOX ®-40 silica binder + PEG pore former. Slow ramp, long denitrification cycle. | 96 | 82 | 5.3 | 1.07 |
| 9 | LUDOX ®-40 silica binder, + Zero PEG, Slow ramp, long denitrification cycle. | 96 | 83 | 5.2 | 1.07 |

[†]% conversion is as defined above and % selectivity is defined above.

Bound MMO-1 Catalyst Performance

ACM Ratio=1.0

A commercially manufactured, silica bound and extruded catalyst was calcined in a large 4" calciner (Example 3) and a screen calciner (Example 4) to determine if there are any significant differences between the two calciners that may indicate scale-up considerations. The commercially manufactured catalyst is an extrudate having a diameter of 1/16" (1.6 mm) and has been bound to give the required crush strength for a tubular reactor. The commercially manufactured catalyst showed a relative catalytic activity comparable to that of a laboratory reference catalyst. The commercially manufactured catalyst showed a slight decrease of 2-3% in selectivity for the 4" calciner and may indicate there is a slight decline in selectivity due to binding of the catalyst. However, the relative catalytic selectivity and activity are still good. The screen calcined extrudate (Example 4) gave good relative catalytic activity and selectivity comparable to the laboratory reference catalyst.

MMO-1 Catalyst Performance

ACM Ratio>2.0

The catalyst of Example 2 showed the performance of a catalyst having an ACM ratio of a 2.27 indicating that a high ratio gives a very low relative catalytic activity of 0.12.

MMO-2 Catalyst Performance

ACM Ratio=1.1

When the MMO catalyst formulations were adjusted to give an excess of molybdenum oxide anions over the metal cations and mixed with a PEG pore former and a silica binder, Example 5, Example 7, Example 8 and Example 9 catalysts, the relative catalytic activity of these catalyst increased dramatically up to 5.3 which is 2 to 2.5 times the relative catalytic activity of the MMO-1 catalyst having an ACM ratio of ~1.0.

Effect of Binders and Pore Formers on Relative Catalytic Activity

The catalysts of Example 5 and Example 9 showed the effect of using a silica binder and pore former on catalyst performance. The catalyst of Example 5 showed an increased relative catalytic activity, when only the ACM ratio of the catalyst was raised from 1.0 to 1.1, in the absence of a silica binder and a PEG pore former. The relative catalytic activity of the Example 5 catalyst was increased by 1.7 times. The relative catalytic activity of the Example 8 catalyst showed the effect of using a silica binder on the relative catalytic activity and showed improved results over the unbound MMO-2 Example 5 catalyst. In the Example 9 catalyst, only the silica binder was used with the catalyst preparation without the PEG pore former. The Example 9 catalyst showed very good relative catalytic activity, indicating that the pore former contributes to the relative catalytic activity and selectivity. The data suggests that catalysts having an increased ACM ratio and a silica binder have significantly higher relative catalytic activity compared to the bound commercial MMO-1 catalyst of Example 3 and Example 4. The data further suggests that an increased ACM ratio and a silica binder may act synergistically to improve relative catalytic activity, while maintaining good selectivity. Binding of the MMO-1 with silica, catalysts of Example 3 and Example 4, did not improve relative catalytic activity as compared to the unbound MMO-1 catalyst of Examples 1. However, binding and adding silica to the MMO-2 formulations of the catalysts of Examples 7 and 8 showed significantly improved relative catalytic activity compared to the catalyst of Example 5, which show improved relative catalytic activity over the MMO-1 catalysts.

The stoichiometry for both the MMO-1 and MMO-2 catalysts are used to calculate the ACM ratio. The MMO-2 catalysts of this invention where prepared with 11 wt. % LUDOX®-40 silica binder and 2 wt. % PEG when present.

Effect of Slower Calcination Temperature Ramp

The catalyst of Example 7 shows that using a denitrification profile with a fast temperature ramp and a short soak time gives a selectivity that is significantly lowered, so calcination conditions are important.

The catalysts of Examples 8 and 9 show that with a sufficiently slow ramp rate of 5° C./min and long soak time of 4.5 hours, a good catalyst is produced. When used with PEG and a silica binder, the calcined MMO-2 gives a very high relative catalytic activity of about 5.3 with good selectivity in the Example 8 catalyst. The Example 9 catalyst is a similar MMO-2 except the PEG pore former was not used and only the LUDOX®-40 silica, indicating that the PEG pore former apparently has a small effect on relative catalytic activity.

MMO-1 v. MMO-2 Catalyst Performance

ACM Ratio=0.95 v. ACM Ratio=1.1

The catalyst of Example 6 shows that the relative catalytic activity is lowered when the ACM ratio is less than one and in this case gives a relative catalytic activity of 1.4. Thus, comparing the unbound catalyst of Example 5 to the unbound catalyst of Example 6, where the only difference between the catalysts is an ACM ratio of 1.1 for the former compared to an ACM ratio of 0.95 for the latter, the catalyst of Example 5 has a relative catalytic activity about 2.6 times higher than the relative catalytic activity of the catalyst of Example 6.

XRD Data of NiMo(Phase 1)/CoMo Oxide Crystalline Phase and Catalytic Activity XRD data suggests that the relative catalytic activity increase may be related to an increase in the formation of the NiMo (phase 1)/CoMo oxide phase (NiMo1/CoMo as indicated in FIGS. 1-3) crystalline phase that form in the catalyst during catalyst preparation, drying and calcination. This crystalline phase is formed from the reaction of the molybdate anion and the nickel and cobalt cations. The increase in this crystalline phase is believed to be due to the reaction of additional molybdate anion ($MoO_4^{2-}$) added to the catalyst formulations with unreacted nickel and cobalt cations. Apparently, in the conventional catalyst formulations, there may be insufficient molybdate anion ($MoO_4^{2-}$) to react with all of the nickel and cobalt cations, even though there is an anion to cation molar ratio of one or stoichiometric ratio. Alternatively, the additional molybdate anion ($MoO_4^{2-}$) may preferentially react with the nickel and cobalt cations increasing the amount of the NiMo (phase 1)/CoMo mixed metal oxide phase.

We have found a direct relationship between the relative catalytic activity and the crystalline phase NiMo1/CoMo obtained through XRD analysis. The relative diffraction peak intensities are shown in FIGS. 1-3 and tabulated in Tables 2-4, respectively.

TABLE 2

Metal Oxide Phase Relative Peak Intensities and Relative Catalytic Activities and Selectivities of a $Mo_{12}W_{0.3}$ Catalyst, a $Mo_{12}W_{0.0}$ Catalyst and a $Mo_{12.3}W_{0.0}$ Catalyst

| Catalyst Composition | $Mo_{12}W_{0.3}$ | $Mo_{12}W_{0.0}$ | $Mo_{12.3}W_{0.0}$ |
|---|---|---|---|
| $MoO_x$ | 2.3 | 2.2 | 2.6 |
| $NiMo_2$ | 8.3 | 10.7 | 6.1 |
| FeMo | 8.6 | 7.6 | 7.9 |
| NiMo1[a]/CoMo | 44.7 | 45.1 | 52.0 |
| BiMo | 36.1 | 34.4 | 31.4 |
| rel. activity | 1.0 | 1.0 | 1.5 |
| rel. selectivity | 0.0 | 0.0 | 1.0 |

[a]NiMo phase oxide

The XRD analyses showed that as the peak intensity of the NiMo1/CoMo mixed oxide phase, related to the concentration of this crystalline phase in the catalyst, increased the relative catalytic activity increased. In FIG. 1, the NiMo1/CoMo peak is higher in the $Mo_{12.3}$ catalyst than the $Mo_{12.0}$ catalyst. Correspondingly, the relative catalytic activity of the $Mo_{12.3}$ catalyst is higher than the $Mo_{12.0}$ stoichiometric catalyst. The relative catalytic selectivity is good in both cases.

TABLE 3

Metal Oxide Phase Relative Peak Intensities and Relative Catalytic Activities and Selectivities v. Digestion Time for a MMO-1 Catalyst

| Catalyst Composition | 1 | 2 | 3 | 4 |
|---|---|---|---|---|
| digest time | 10 hour | 5 hour | 2 hour | 0 hour |
| $MoO_x$ | 1.7 | 2.7 | 2.2 | 1.1 |
| $NiMo_2$ | 4.2 | 6.6 | 10.1 | 11.4 |
| FeMo | 6.7 | 5.6 | 10.8 | 10.6 |
| NiMo1[a]/CoMo | 59.6 | 58.1 | 42.9 | 41.5 |
| BiMo | 27.8 | 27.0 | 34.0 | 35.4 |
| rel. activity | 1.1 | 1.1 | 0.7 | 0.3 |
| rel. selectivity | 0.0 | 0.0 | — | — |

[a]NiMo phase 1 oxide

In FIG. 2, the results of an experiment are shown in which, during preparation, samples were taken during wet chemical synthesis at 0 hr, 2 hr, 5 hr, and 10 hr after the digestion period was started. The digestion period occurs during wet chemical synthesis immediately after all the chemical reagents are added. The results show the NiMo1/CoMo crystalline phase develops over time and the higher the phase concentration, the higher the relative catalytic activity. Looking at the data in Table 3, the relative catalytic activity is 0.3 for a digestion time of 0 hours, while the relative catalytic activity is 1.1 for a digestion time of 5 and 10 hours.

TABLE 4

Metal Oxide Phase Relative Peak Intensities and Relative Catalytic Activities and Selectivities of a MMO-1 Catalyst Compared to an MMO-2 Catalyst

| | Catalyst Type | |
|---|---|---|
| | MMO-1 | MMO-2 |
| $MoO_x$ | 3.7 | — |
| $NiMo_2$ | 9.6 | — |
| FeMo | 7.7 | 7.7 |
| NiMo1[a]/CoMo | 47.1 | 53.5 |
| BiMo | 31.9 | 28.1 |
| rel. activity | 1.1 | 2.0-2.5 |
| rel. selectivity | 0.0 | 0.0 |

[a]NiMo phase oxide

FIG. 3 shows a consistent trend in which the more NiMo1/CoMo crystalline phase present, the higher the relative catalytic activity. The MMO-2 catalyst, which has an ACM ratio 1.1, but less than 2.0, had a relative catalytic activity of 2 to 2.5 times the MMO-1 catalyst, which has an ACM ratio of ≤1.0. The intensity of the MMO-1 peak is the same intensity as presented in FIGS. 1 and 2.

Additional support for the relationship between relative catalytic activity and the NiMo1/CoMo crystalline phase is tabulated in Table 5. In this experiment, a portion of the slurry is withdrawn after the 10 hr digestion step and the mother liquor is filtered off leaving a filter cake. It is known that the mother liquor contains the water soluble divalent metals Ni, Co, Mg, and Zn leaving the filter cake without these metals.

The filter cake is processed as normal including drying, forming, and calcination using a typical MMO-1 preparation. Due to the absence of divalent metals in the catalyst, there is very little or no NiMo1/CoMo crystalline phase present. The corresponding relative catalytic activity is 0.12 compared to the 1.0 relative catalytic activity for a regular MMO-1 catalyst and the ACM ratio is 2.27.

TABLE 5

Relative Catalytic Activity of a Catalyst Having an ACM Ratio of 2.27

| Sample | Relative Activity | ACM Ratio | % Metals | | | | | | | |
|---|---|---|---|---|---|---|---|---|---|---|
| | | | Mo | W | Bi | Fe | Co | Mg | Zn | Cs |
| Reference | 1.1 | 1 | 38 | 1.96 | 7 | 4.2 | 3.7 | 0.44 | 1.22 | 2.6 |
| Filtered | 0.12 | 2.27 | 46 | 2.3 | 8.4 | 4.8 | 0.027 | 0.0005 | 0.005 | 2.5 |

Model to Explain Higher NiMo1/CoMo Crystalline Phase

While not meaning to be bound by any explanation for the increase relative catalytic activity achieved by increasing the ACM ratio, we believe that when a small amount of molybdate is added to the catalyst formulation, there is a better opportunity to react all of the divalent metals to form the mixed oxides such as $NiMoO_4$, $CoMoO_4$, $MgMoO_4$, and $ZnMoO_4$ on calcination. It is thought that the divalent metals are laid down on top of the other metal molybdates during catalyst preparation. It is known that too much molybdate results in an excess of molybdenum trioxide ($MoO_3$), which is detrimental to this olefin oxidation reaction. Likewise, if there is not enough molybdenum, then there is an excess of divalent metals and a reduction in the mixed oxides such as $NiMoO_4$, $CoMoO_4$, $MgMoO_4$, and $ZnMoO_4$, which is known also to be detrimental to catalyst performance. It is believed that for the Mo mixed metal oxides of the present invention, the levels of $MoO_3$, upon continued additions of Mo, become sufficiently high such that catalyst activity enhancements realized through the formation of the preferred crystal phase are offset by the negative effects on catalyst activity by $MoO_3$. This is believed to occur at a ACM values of 2.00 and higher.

The catalysts of this invention are uniquely defined and distinguished over prior art catalysts with respect to the anion to cation molar (ACM) ratio defining an aspect of the stoichiometry of the catalysts of this invention. Most broadly, the catalysts of this invention have an ACM ratio of greater than 1.00 and less than 2.00 (preferably greater than 1.06 and less than 2.00) through the addition of Mo so that the Mo mole ratio is higher than the ratio of trivalent, divalent and monovalent metal cation present in the catalyst. Thus, the catalysts of this invention were prepared with an Mo content of 12.9 instead of 12.0, with the other metal components in the catalyst kept at similar molar concentrations yielding catalysts with surprisingly increased relative catalytic activity. It is our belief that the additional molybdenum above stoichiometric amounts in the catalyst, increases the formation of nickel and cobalt molybdates, which in turn dramatically increases relative catalytic activity. However, if the molybdenum is increased too much then other crystalline phases may form, which actually lowers relative catalytic activity.

The particularly dramatic increase in relative catalytic activity resulting from adjusting the ACM ratio to a value greater than 1.00, but less than 2.00, while maintaining an M' to M molar ratio between 1.95 and 2.15, by adding an additional amount of molybdenum above a stoichiometric amount (i.e., the amount of molybdenum or molybdenum and tungsten to produce a catalyst having an ACM ratio of 1.0) was unexpected. The prior art showed that catalyst compositions having an ACM ratio less than 1.0 had decreased relative catalytic activity relative to a catalyst composition having an ACM ratio of 1.0, while experiments performed herein showed that catalyst compositions having an ACM ratio greater than or equal to 2.0 also had decreased relative catalytic activity. On the other hand, we discovered a regime of particularly highly active catalyst compositions, where the catalyst compositions are characterized by having an ACM ratio≥1.06 and <2.0 and an M' to M molar ratio between 1.95 and 2.15. The desired ACM ratio is brought about by adding a relatively small additional amount of molybdenum to the catalyst compositions, while maintaining the M' to M molar ratio. This relatively small increased amount of molybdenum is believed to result in a measurable increase in the formation of divalent metal mixed molybdates such as nickel and cobalt mixed molybdates. While not intending to be bound by an theory, the inventors believe that this relatively small increased amount of molybdenum in the catalyst compositions, while maintaining the M' to M molar ratio in its specified range, and the corresponding increase in divalent metal mixed molybdates is likely responsible for the significant increase in relative catalytic activity up to 2.5 times compared to catalyst composition having ACM ratios and the M' to M molar ratios outside of these specified values, i.e., (1) 1.00<ACM ratio<2.00 and (2) an M' to M molar ratio between 1.95 and 2.15. The inventors believe that the addition of the relatively small additional amount of molybdenum permits a more complete reaction of molybdate with the divalent metal M' such as nickel and cobalt to produce corresponding mixed nickel cobalt molybdates, while the addition of too much molybdenum, reduces relative catalytic activity due to the formation of other less catalytically active crystalline phases.

Figure 4:
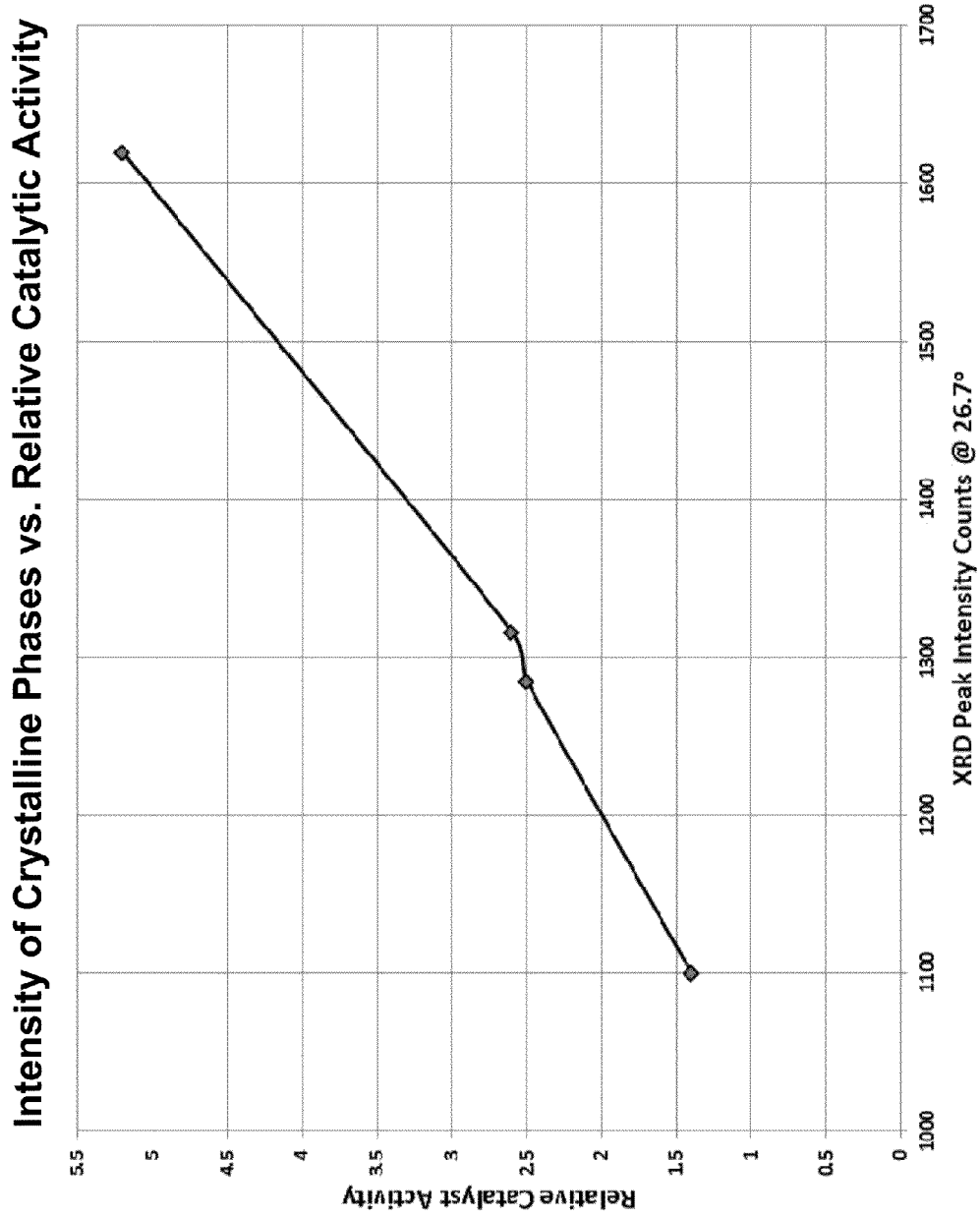
FIG. 4 depicts a graph of the concentration of the crystalline phase $NiMoO_4$ (phase1)/$CoMoO_4$ (NiMo1/CoMo) versus relative catalytic activity.

FIG. 4 shows the relationship between the concentration of the $NiMoO_4$ (phase 1)/$CoMoO_4$ represented by the relative XRD peak intensity counts observed at 26.7 degrees and the increase in relative catalytic activity. As the concentration of the $NiMoO_4$ (phase 1)/$CoMoO_4$ increases the catalyst activity increases. We believe the relative catalytic activity increases due to better overall reaction between the molybdenum and the nickel and cobalt oxides to form more of the catalytically active mixed metal molybdates, which results from having a little more molybdenum around to react with the nickel and cobalt oxides.

Figure 5:
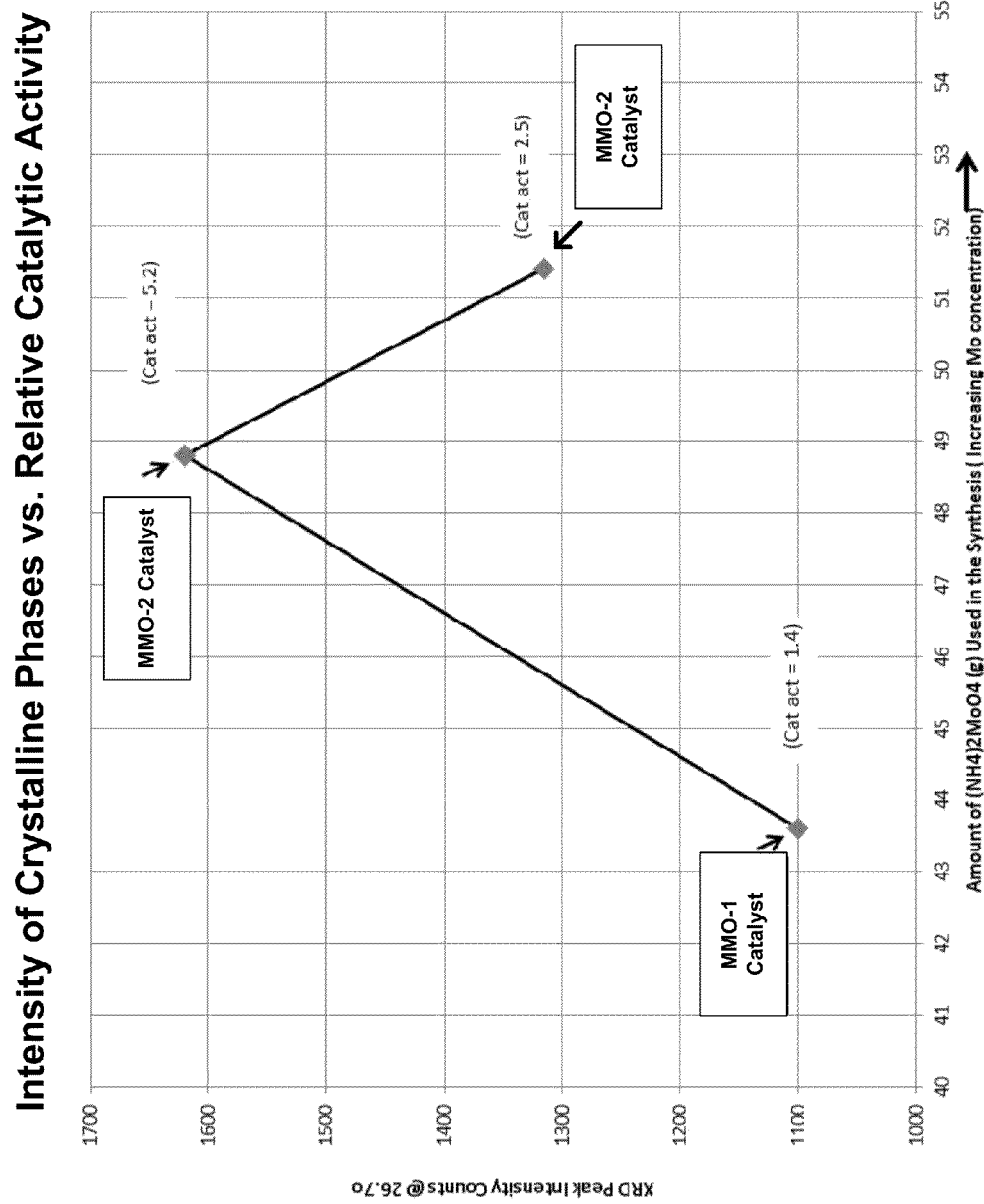
FIG. 5 depicts a graph showing that as the molybdenum concentration is increased in the catalyst, the $NiMoO_4$ (phase1)/$CoMoO_4$ (NiMo1/CoMo) crystalline phase composition initially increases to a maximum and then decreases.

FIG. 5 shows that just increasing the molybdenum concentration in the catalyst does not necessarily lead to a higher activity catalyst. FIG. 5 shows that as the molybdenum is increased in the catalyst (represented by grams of $(NH_4)_2MoO_4$ in the catalyst recipe) the crystalline phase $NiMoO_4$ (phase 1)/$CoMoO_4$ (sometime referred to herein as NiMo1/CoMo) increases up to a maximum at $Mo_{12.9}$, but then decreases as the molybdenum concentration in the catalyst increases. It is not known for certain why this happens, but the most likely cause is because the formation of another crystalline phase is favored as the molybdenum concentration increases above about 49 g of $(NH_4)_2MoO_4$ in the catalysts recipe which is less catalytically active. The MMO-2 catalyst of FIG. 5, having a catalytic activity of 2.5 (the data point on the far right) does not appear in Table 1; this specific catalyst has an ACM value of 1.12.

The invention also includes a process for the gas phase catalytic oxidation of an olefin to an aldehyde, the process comprising:

contacting an olefin and a molecular oxygen-containing gas to form an unsaturated aldehyde in the presence of a catalyst comprising a mixed metal oxide of formula (I):

$$Mo_aW_bM_cM'_dM''_eZ_fO_g \quad (I)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.0 and 0.4;
c is a number between 2.0 and 4.0;
d is a number between 5.0 and 8.0;
e is a number between 0.5 and 1.5,
f is a number between 0.5 and 1.5; and
g is a number that completes the valency of the formula, wherein the mixed metal oxide has:
an anion to cation molar (ACM) ratio greater than 1.00 and less than 2.00; and
an M' to M molar ratio is between 1.95 and 2.15, and wherein
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3c+2d+e)$, and
recovering a product stream comprising an aldehyde.

Various embodiments of the process include a catalyst comprising mixed metal oxides of any and all of formulas (II)-(VI), as well, as any and all of the ranges of ACM ratio and M' to M molar ratio discussed throughout this disclosure. Various other steps, known in the art of olefin oxidation to aldehydes using mixed metal oxide, may also be included, as may be useful in particular embodiments, as recognized by the skilled artisan.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A catalyst for the oxidation of an olefin to an unsaturated aldehyde comprising a mixed metal oxide having the formula (I):

$$Mo_aW_bM_cM'_dM''_eZ_fO_g \quad (I)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and/or mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.0 and 0.4;
c is a number between 2.0 and 4.0;
d is a number between 5.0 and 8.0;
e is a number between 0.5 and 1.5;
f is a number between 0.5 and 1.5; and
g is a number that completes the valency of the formula;
wherein the mixed metal oxide has:
an anion to cation molar (ACM) ratio greater than 1.00 and less than 2.00; and
an M' to M molar ratio between 1.95 and 2.15, and wherein
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3c+2d+e)$.

2. The catalyst of claim 1, wherein the M' to M molar ratio is between 2.00 and 2.10.

3. The catalyst of claim 2, wherein the M' to M molar ratio is 2.06.

4. The catalyst of claim 1, wherein the ACM ratio is greater than 1.00 and less than 1.80.

5. The catalyst of claim 4, wherein the ACM ratio is greater than 1.00 and less than 1.60.

6. The catalyst of claim 5, wherein the ACM ratio is greater than 1.00 and less than 1.40.

7. The catalyst of claim 6, wherein the ACM ratio is greater than 1.00 and less than 1.20.

8. The catalyst of claim 7, wherein the ACM ratio is greater than or equal to 1.06 and less than 1.20.

9. The catalyst of claim 1, wherein the mixed metal oxide further has a $[Mo]_{res}$ between 0.4 and less than 2.0.

10. The catalyst of claim 9, wherein $[Mo]_{res}$ is 0.9.

11. The catalyst of claim 1, further comprising from 1 wt. % to 20 wt. % of a silica binder and from 0.1 wt. % to 5 wt. % of a pore former, where the wt. % is based on the total weight of the catalyst.

12. The catalyst of claim 1, wherein the catalyst comprises a mixed metal oxide having the formula (II):

$$Mo_aW_bBi_{c1}Fe_{c2}M_{c3}M'_dM''_eZ_fO_g \quad (II)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d is a number between 5.0 and 8.0;
e is a number between 0.5 and 1.5;
f is a number between 0.5 and 1.5; and
g is a number that completes the valency of the formula,
wherein Bi and Fe in formula (II) are in their plus three oxidation states,
wherein the mixed metal oxide has:
an anion to cation molar (ACM) ratio greater than 1.00 and less than 2.00; and
an M' to M molar ratio between 1.95 and 2.15, and
wherein
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3(c1+c2+c3)+2d+e)$.

13. The catalyst of claim 12, further comprising from 1 wt. % to 20 wt. % of a silica binder and from 0.1 wt. % to 5 wt. % of a pore former, where the wt. % is based on the total weight of the catalyst.

14. The catalyst of claim 1, wherein the catalyst comprises a mixed metal oxide having the formula (III):

$$Mo_aW_bBi_{c1}Fe_{c2}M_{c3}Ni_{d1}Co_{d2}M'_{d3}M''_eZ_fO_g \quad (III)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2 and d3 sum to a number between 5.0 and 8.0;
e is a number between 0.5 and 1.5;
f is a number between 0.5 and 1.5; and
g is a number that completes the valency of the formula,
wherein Bi and Fe in formula (III) are in their plus three oxidation states and Ni and Co in formula (III) are in their plus two oxidation states,
wherein the mixed metal oxide has:
an anion to cation molar (ACM) ratio greater than 1.00 and less than 2.00; and
an M' to M molar ratio between 1.95 and 2.15, and
wherein
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3(c1+c2+c3)+2(d1+d2+d3)+e)$.

15. The catalyst of claim 14, further comprising from 1 wt. % to 20 wt. % of a silica binder and from 0.1 wt. % to 5 wt. % of a pore former, where the wt. % is based on the total weight of the catalyst.

16. The catalyst of claim 1, wherein the catalyst comprises a mixed metal oxide having the formula (IV):

$$Mo_aW_bBi_{c1}Fe_{c2}M_{c3}Ni_{d1}Co_{d2}Mg_{d3}M'_{d4}M''_eZ_fO_g \quad (IV)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2, d3 and d4 sum to a number between 5.0 and 8.0;
e is a number between 0.5 and 1.5;
f is a number between 0.5 and 1.5; and
g is a number that completes the valency of the formula,
wherein Bi and Fe in formula (IV) are in their plus three oxidation states and Ni, Co, and Mg in formula (IV) are in their plus two oxidation states,
wherein the mixed metal oxide has:
an anion to cation molar (ACM) ratio greater than 1.00 and less than 2.00; and
an M' to M molar ratio between 1.95 and 2.15, and
wherein
the ACM ratio is defined as $(2\times[Mo]+2\times[W])$ to $(3\times[M']+2\times[M]+[M''])$ or $(2\times[Mo]+2\times[W])/(3\times[M]+2\times[M']+[M''])$ or $2(a+b)/(3(c1+c2+c3)+2(d1+d2+d3+d4)+e)$.

17. The catalyst of claim 16, further comprising from 1 wt. % to 20 wt. % of a silica binder and from 0.1 wt. % to 5 wt. % of a pore former, where the wt. % is based on the total weight of the catalyst.

18. The catalyst of claim 1, wherein the catalyst comprises a mixed metal oxide having the formula (V):

$$Mo_aW_bBi_{c1}Fe_{c2}M_{c3}Ni_{d1}Co_{d2}Mg_{d3}Zn_{d4}M'_{d5}Cs_{e1}M''_{e2}Z_fO_g \quad (V)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;

M" is a monovalent metal selected from the group consisting of alkali metals, monovalent transition metals, and mixtures thereof;

Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;

a is a number between 12.3 and 14.0;
b is a number between 0.2 and 0.4;
c1, c2 and c3 sum to a number between 2.0 and 4.0;
d1, d2, d3, d4, and d5 sum to a number between 5.0 and 8.0;
e1 and e2 sum to a number between 0.5 and 1.5;
f is a number between 0.5 and 1.5; and
g is a number that completes the valency of the formula, wherein Bi and Fe in formula (V) are in their plus three oxidation states, Ni, Co, Mg and Zn in formula (V) are in their plus two oxidation states and Cs in formula (V) is in its plus one oxidation state, wherein the mixed metal oxide has:
an anion to cation molar (ACM) ratio greater than 1.00 and less than 2.00, and
an M' to M molar ratio between 1.95 and 2.15, and
wherein
the ACM ratio is defined as $(2\times[Mo]+2\times[W])$ to $(3\times[M]+2\times[M']+[M"])$ or $(2\times[Mo]+2\times[W])/(3\times[M]+2\times[M']+[M"])$ or $2(a+b)/(3(c1+c2+c3)+2(d1+d2+d3+d4+d5)+(e1+e2))$.

19. The catalyst of claim 18, further comprising from 1 wt. % to 20 wt. % of a silica binder and from 0.1 wt. % to 5 wt. % of a pore former, where the wt. % is based on the total weight of the catalyst.

20. The catalyst of claim 1, wherein the catalyst comprises a mixed metal oxide having the formula (VI):

$$Mo_aW_bBi_{c1}Fe_{c2}M_{c3}Ni_{d1}Co_{d2}Mg_{d3}Zn_{d4}M'_{d5}Cs_{e1}M"_{e2}Sb_{f1}Z_{f2}O_g \quad (VI)$$

where:
M is a trivalent metal selected from the group consisting of bismuth (Bi), trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2, d3, d4, and d5 sum to a number between 5.0 and 8.0;
e1 and e2 sum to a number between 0.5 and 1.5;
f1 and f2 sum to a number between 0.5 and 1.5; and
g is a number that completes the valency of the formula, wherein Bi and Fe in formula (VI) are in their plus three oxidation states, Ni, Co, Mg and Zn in formula (VI) are in their plus two oxidation states and Cs in formula (VI) is in its plus one oxidation state, wherein the mixed metal oxide has:
an anion to cation molar (ACM) ratio greater than 1.00 and less than 2.00; and
an M' to M molar ratio between 1.95 and 2.15, and
wherein
the ACM ratio is defined as $(2\times[Mo]+2\times[W])$ to $(3\times[M]+2\times[M']+[M"])$ or $(2\times[Mo]+2\times[W])/(3\times[M]+2\times[M']+[M"])$ or $2(a+b)/(3(c1+c2+c3)+2(d1+d2+d3+d4+d5)+(e1+e2))$.

21. The catalyst of claim 20, further comprising from 1 wt. % to 20 wt. % of a silica binder and from 0.1 wt. % to 5 wt. % of a pore former, where the wt. % is based on the total weight of the catalyst.

22. The catalyst of claim 1, wherein the mixed metal oxide further has an enhanced relative XRD peak corresponding to a NiMo (phase 1)/CoMo mixed oxide phase compared to a mixed metal oxide not meeting one or both of the following conditions:
(1) an ACM ratio greater than or equal to 1.06 and less than 1.20 and
(2) an M' to M molar ratio between 1.95 and 2.15.

23. The catalyst of claim 1, wherein the mixed metal oxide is characterized in that an intensity of a relative XRD peak corresponding to a NiMo (phase 1)/CoMo mixed oxide phase is increased compared to a mixed metal oxide not meeting one or both of the following conditions:
(1) an ACM ratio greater than or equal to 1.06 and less than 1.20 and
(2) an M' to M molar ratio between 1.95 and 2.15.

24. A process for the gas phase catalytic oxidation of an olefin to an aldehyde comprising:
contacting an olefin and a molecular oxygen-containing gas to form an unsaturated aldehyde in the presence of a catalyst comprising a mixed metal oxide having the formula (I):

$$Mo_aW_bM_cM'_dM"_eZ_fO_g \quad (I)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.0 and 0.4;
c is a number between 2.0 and 4.0;
d is a number between 5.0 and 8.0;
e is a number between 0.5 and 1.5,
f is a number between 0.5 and 1.5; and
g is a number that completes the valency of the formula,
wherein the mixed metal oxide has:
an anion to cation molar (ACM) ratio greater than 1.00 and less than 2.00; and
an M' to M molar ratio between 1.95 and 2.15, and
wherein
the ACM ratio is defined as $(2\times[Mo]+2\times[W])$ to $(3\times[M]+2\times[M']+[M"])$ or $(2\times[Mo]+2\times[W])/(3\times[M]+2\times[M']+[M"])$ or $2(a+b)/(3c+2d+e)$, and
recovering a product stream comprising an aldehyde.

25. The process of claim 24, wherein the catalyst further comprises from 1 wt. % to 20 wt. % of a silica binder and from 0.1 wt. % to 5 wt. % of a pore former, where the wt. % is based on the total weight of the catalyst.

26. The process of claim 24, wherein the catalyst comprises a mixed metal oxide having the formula (II):

$$Mo_aW_bBi_{c1}Fe_{c2}M_{c3}M'_dM''_eZ_fO_g \quad (II)$$

where:
M is a trivalent metal selected from the group consisting of trivalent transition metals, trivalent non-transition metals and mixtures thereof,
M' is a divalent metal selected from the group consisting of alkaline earth metals, divalent transition metals, divalent non-transition metals, and mixtures thereof,
M" is a monovalent metal selected from the group consisting of alkali metals, monovalent transition metals, and mixtures thereof,
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof,
a is a number between 12.3 and 14.0;
b is a number between 0.2 and 0.4;
c1, c2 and c3 sum to a number between 2.0 and 4.0;
d is a number between 5.0 and 8.0;
e is a number between 0.5 and 1.5;
f is a number between 0.5 and 1.5;
g is a number that completes the valency of the formula,
wherein Bi and Fe in formula (II) are in their plus three oxidation states,
wherein the mixed metal oxide has:
an anion to cation molar (ACM) ratio greater than 1.00 and less than 2.00; and
an M' to M molar ratio between 1.95 and 2.15, and
wherein
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3(c1+c2+c3)+2d+e)$.

27. The process of claim 26, wherein the catalyst further comprises from 1 to 20 wt. % of a silica binder and from 0.1 to 5 wt. % of a pore former, where the wt. % is based on the total weight of the catalyst.

28. The process of claim 24, wherein the catalyst comprises a mixed metal oxide having the formula (III):

$$Mo_aW_bBi_{c1}Fe_{c2}M_{c3}Ni_{d1}Co_{d2}M'_{d3}M''_eZ_fO_g \quad (III)$$

where:
M is a trivalent metal selected from the group consisting of trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2 and d3 sum to a number between 5.0 and 8.0;
e is a number between 0.5 and 1.5;
f is a number between 0.5 and 1.5;
g is a number that completes the valency of the formula;
wherein Bi and Fe in formula (III) are in their plus three oxidation states, Ni, Co, and Mg in formula (III) are in their plus two oxidation states,
wherein the mixed metal oxide has:
an anion to cation molar (ACM) ratio greater than 1.00 and less than 2.00; and
an M' to M molar ratio between 1.95 and 2.15; and
wherein
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3(c1+c2+c3)+2(d1+d2+d3)+e)$.

29. The process of claim 28, wherein the catalyst further comprises from 1 to 20 wt. % of a silica binder and from 0.1 to 5 wt. % of a pore former, where the wt. % is based on the total weight of the catalyst.

30. The process of claim 24, wherein the catalyst comprises a mixed metal oxide having the formula (IV):

$$Mo_aW_bBi_{c1}Fe_{c2}M_{c3}Ni_{d1}Co_{d2}Mg_{d3}M'_{d4}M''_eZ_fO_g \quad (IV)$$

where:
M is a trivalent metal selected from the group consisting of bismuth (Bi), trivalent transition metals, trivalent non-transition metals and mixtures thereof;
M' is a divalent metal selected from the group consisting of alkaline earth metals, divalent transition metals, divalent non-transition metals, and mixtures thereof;
M" is a monovalent metal selected from the group consisting of alkali metals, monovalent transition metals, and mixtures thereof;
Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;
a is a number between 12.3 and 14.0;
b is a number between 0.2 and 0.4;
c1, c2 and c3 sum to a number between 2.0 and 4.0;
d1, d2, d3, and d4 sum to a number between 5.0 and 8.0;
e is a number between 0.5 and 1.5;
f is a number between 0.5 and 1.5; and
g is a number that completes the valency of the formula,
wherein Bi and Fe in formula (IV) are in their plus three oxidation states, Ni, Co, and Mg in formula (IV) are in their plus two oxidation states,
wherein the mixed metal oxide has:
an anion to cation molar (ACM) ratio greater than 1.00 and less than 2.00; and
an M' to M molar ratio between 1.95 and 2.15, and
wherein
the ACM ratio is defined as $(2\times[Mo]+2\times[W])$ to $(3\times[M]+2\times[M']+[M''])$ or $(2\times[Mo]+2\times[W])/(3\times[M]+2\times[M']+[M''])$ or $2(a+b)/(3(c1+c2+c3)+2(d1+d2+d3+d4)+e)$.

31. The process of claim 30, wherein the catalyst further comprises from 1 to 20 wt. % of a silica binder and from 0.1 to 5 wt. % of a pore former, where the wt. % is based on the total weight of the catalyst.

32. The process of claim 24, wherein the catalyst comprises a mixed metal oxide having the formula (V):

$$Mo_aW_bBi_{c1}Fe_{c2}M_{c3}Ni_{d1}Co_{d2}Mg_{d3}Zn_{d4}M'_{d5}Cs_{e1}M''_{e2}Z_fO_g \quad (V)$$

where:
M is a trivalent metal selected from the group consisting of bismuth (Bi), trivalent transition metals, trivalent non-transition metals and mixtures thereof;

M' is a divalent metal selected from the group consisting of alkaline earth metals, divalent transition metals, divalent non-transition metals, and mixtures thereof;

M" is a monovalent metal selected from the group consisting of alkali metals, monovalent transition metals, and mixtures thereof;

Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;

a is a number between 12.3 and 14.0;
b is a number between 0.2 and 0.4;
c1, c2 and c3 sum to a number between 2.0 and 4.0;
d1, d2, d3, d4, and d5 sum to a number between 5.0 and 8.0;
e1 and e2 sum to a number between 0.5 and 1.5;
f is a number between 0.5 and 1.5; and
g is a number that completes the valency of the formula, wherein Bi and Fe in formula (V) are in their plus three oxidation states, Ni, Co, Mg and Zn in formula (V) are in their plus two oxidation states and Cs in formula (V) is in its plus one oxidation state, wherein the mixed metal oxide has:
an anion to cation molar (ACM) ratio greater than 1.00 and less than 2.00; and
an M' to M molar ratio between 1.95 and 2.15, and wherein
the ACM ratio is defined as $(2\times[Mo]+2\times[W])$ to $(3\times[M]+2\times[M']+[M"])$ or $(2\times[Mo]+2\times[W])/(3\times[M]+2\times[M']+[M"])$ or $2(a+b)/(3(c1+c2+c3)+2(d1+d2+d3+d4+d5)+(e1+e2))$.

33. The process of claim 32, wherein the catalyst further comprises from 1 wt. % to 20 wt. % of a silica binder and from 0.1 wt. % to 5 wt. % of a pore former, where the wt. % is based on the total weight of the catalyst.

34. The process of claim 24, wherein the catalyst comprises a mixed metal oxide having the formula (VI):

$$Mo_aW_bBi_{c1}Fe_{c2}M_{c3}Ni_{d1}Co_{d2}Mg_{d3}Zn_{d4}M'_{d5}Cs_{e1}M"_{e2}Sb_{f1}Z_{f2}O_g \quad (VI)$$

where:
M is a trivalent metal selected from the group consisting of bismuth (Bi), trivalent transition metals, trivalent non-transition metals and mixtures thereof;

M' is a divalent metal selected from the group consisting of alkaline earth metals, divalent transition metals, divalent non-transition metals, and or mixtures thereof;

M" is a monovalent metal selected from the group consisting of alkali metals, monovalent transition metals, and mixtures thereof;

Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;

a is a number between 12.3 and 14.0;
b is a number between 0.2 and 0.4;
c1, c2 and c3 sum to a number between 2.0 and 4.0;
d1, d2, d3, d4, and d5 sum to a number between 5.0 and 8.0;
e1 and e2 sum to a number between 0.5 and 1.5;
f1 and f2 sum to a number between 0.5 and 1.5; and
g is a number that completes the valency of the formula, wherein Bi and Fe in formula (VI) are in their plus three oxidation states, Ni, Co, Mg and Zn in formula (VI) are in their plus two oxidation states and Cs in formula (VI) is in its plus one oxidation state, wherein the mixed metal oxide has:
an anion to cation molar (ACM) ratio greater than 1.00 and less than 2.00; and
an M' to M molar ratio between 1.95 and 2.15, and wherein
the ACM ratio is defined as $(2\times[Mo]+2\times[W])$ to $(3\times[M]+2\times[M']+[M"])$ or $(2\times[Mo]+2\times[W])/(3\times[M]+2\times[M']+[M"])$ or $2(a+b)/(3(c1+c2+c3)+2(d1+d2+d3+d4+d5)+(e1+e2))$.

35. The process of claim 34, wherein the catalyst further comprises from 1 wt. % to 20 wt. % of a silica binder and from 0.1 wt. % to 5 wt. % of a pore former, where the wt. % is based on the total weight of the catalyst.

36. The process of claim 24, wherein the mixed metal oxide further has an enhanced relative XRD peak corresponding to a NiMo (phase 1)/CoMo mixed oxide phase compared to a mixed metal oxide not meeting one or both of the following conditions:
(1) an ACM ratio greater than or equal to 1.06 and less than 1.20 and
(2) an M' to M molar ratio between 1.95 and 2.15.

37. The process of claim 24, wherein the mixed metal oxide is characterized in that an intensity of a relative XRD peak corresponding to a NiMo (phase 1)/CoMo mixed oxide phase is increased compared to a mixed metal oxide not meeting one or both of the following conditions:
(1) an ACM ratio greater than or equal to 1.06 and less than 1.20 and
(2) an M' to M molar ratio between 1.95 and 2.15.

38. A mixed metal oxide having the formula (I):

$$Mo_aW_bM_cM'_dM"_eZ_fO_g \quad (I)$$

where:
M is a trivalent metal selected from the group consisting of trivalent transition metals, trivalent non-transition metals and mixtures thereof;

M' is a divalent metal selected from the group consisting of alkaline earth metals, divalent transition metals, divalent non-transition metals, and or mixtures thereof;

M" is a monovalent metal selected from the group consisting of alkali metals, monovalent transition metals, and mixtures thereof;

Z is an element in the form of an oxide when added to a pre-catalyst preparation and is selected from the group consisting of cerium, antimony, phosphorus, boron, sulfur, silicon, aluminum, titanium, tellurium, vanadium, zirconium, niobium, and mixtures thereof;

a is a number between 12.3 and 14.0;
b is a number between 0.0 and 0.4;
c is a number between 2.0 and 4.0;
d is a number between 5.0 and 8.0;
e is a number between 0.5 and 1.5;
f is a number between 0.5 and 1.5; and
g is a number that completes the valency of the formula;

wherein the mixed metal oxide has:
an anion to cation molar (ACM) ratio greater than 1.00 and less than 2.00; and
an M' to M molar ratio between 1.95 and 2.15, and wherein
the ACM ratio is defined as $(2\times[Mo]+2\times[W])$ to $(3\times[M]+2\times[M']+[M"])$ or $(2\times[Mo]+2\times[W])/(3\times[M]+2\times[M']+[M"])$ or $2(a+b)/(3c+2d+e)$.

* * * * *